United States Patent
Barnicki et al.

(10) Patent No.: US 10,544,077 B2
(45) Date of Patent: Jan. 28, 2020

(54) PROCESS FOR MAKING FORMIC ACID UTILIZING HIGHER-BOILING FORMATE ESTERS

(71) Applicant: Eastman Chemical Company, Kingsport, TN (US)

(72) Inventors: Scott Donald Barnicki, Kingsport, TN (US); Robert Thomas Hembre, Johnson City, TN (US); Sumit Chakraborty, Johnson City, TN (US); Vickie Haygood Osborne, Fall Branch, TN (US); Michael Richard Laningham, Erwin, TN (US); Stijn Van de Vyver, Ghent (BE)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/043,329

(22) Filed: Jul. 24, 2018

(65) Prior Publication Data

US 2019/0039985 A1   Feb. 7, 2019

Related U.S. Application Data

(60) Provisional application No. 62/540,343, filed on Aug. 2, 2017.

(51) Int. Cl.
   *C07C 51/09*   (2006.01)
   *C07C 51/12*   (2006.01)
   *C07C 51/44*   (2006.01)
   *C07C 51/46*   (2006.01)

(52) U.S. Cl.
   CPC .............. *C07C 51/09* (2013.01); *C07C 51/12* (2013.01); *C07C 51/44* (2013.01); *C07C 51/46* (2013.01)

(58) Field of Classification Search
   CPC ......... C07C 51/09; C07C 51/12; C07C 51/44; C07C 51/46; C07C 53/02
   See application file for complete search history.

(56) References Cited

U.S. PATENT DOCUMENTS

| | | |
|---|---|---|
| 1,400,195 A | 12/1921 | Willkie |
| 1,857,921 A | 5/1932 | Lazier |
| 1,999,403 A | 4/1935 | Dreyfus |
| 2,060,880 A | 11/1936 | Lazier |
| 2,152,182 A | 3/1939 | Ellis et al. |
| 2,305,104 A | 12/1942 | Pardee, Jr. |
| 2,504,497 A | 4/1950 | Charles et al. |
| 2,607,805 A | 8/1952 | Gresham |
| 3,907,884 A | 9/1975 | Lynn et al. |
| 3,911,003 A | 10/1975 | Suzuki |
| 4,052,424 A | 10/1977 | Vanderspurt |
| 4,076,594 A | 2/1978 | Buelow et al. |
| 4,112,245 A | 9/1978 | Zehner et al. |
| 4,149,009 A | 4/1979 | Yoneoka et al. |
| 4,214,106 A | 7/1980 | Freudenberger et al. |
| 4,216,339 A | 8/1980 | Couteau et al. |
| 4,217,460 A | 8/1980 | Hohenschutz et al. |
| 4,218,568 A | 8/1980 | Hohenschutz et al. |
| 4,232,171 A | 11/1980 | Yoneoka et al. |
| 4,319,037 A | 3/1982 | Yoneoka |
| 4,326,073 A * | 4/1982 | Wolf .................... C07C 51/09 203/84 |
| 4,366,333 A | 12/1982 | Wilkes |
| 4,436,835 A | 3/1984 | Horie et al. |
| 4,440,873 A | 4/1984 | Miyazaki et al. |
| 4,453,026 A | 6/1984 | Tahara et al. |
| 4,480,122 A | 10/1984 | Horlenko et al. |
| 4,511,744 A | 4/1985 | Miyazaki et al. |
| 4,601,909 A | 7/1986 | Nagoshi |
| 4,677,234 A | 6/1987 | Bartley |
| 4,792,620 A | 12/1988 | Paulik et al. |
| 5,144,062 A | 9/1992 | Chen et al. |
| 5,194,675 A | 3/1993 | Joerg et al. |
| 5,206,433 A | 4/1993 | Hohenschutz et al. |
| 6,376,723 B2 | 4/2002 | Drent et al. |
| 6,455,742 B1 | 9/2002 | Cortright et al. |
| 6,841,085 B2 | 1/2005 | Werpy et al. |
| 6,956,134 B2 | 10/2005 | Liu et al. |
| 7,615,671 B2 | 11/2009 | Puckette et al. |

(Continued)

FOREIGN PATENT DOCUMENTS

CA   1 238 919 A   7/1988
EP   2 599 544 A1   6/2013

(Continued)

OTHER PUBLICATIONS

Chintan et al., "Separation of azeotropic mixture of formic aci-water by using Li—Br as a salt by extractive distillation," IJARIIE-SSN, vol. 2, Issue 3, 2016. (Year: 2016).*
Notice of Allowance dated Mar. 7, 2019 received in U.S. Appl. No. 16/043,317.
Notice of Allowance dated Mar. 7, 2019 received in U.S. Appl. No. 16/043,320.
Notice of Allowance dated Jun. 5, 2019 received in co-pending U.S. Appl. No. 16/043,308.
Office Action dated Jun. 14, 2019 received in U.S. Appl. No. 16/043,324.
Co-pending U.S. Appl. No. 16/043,303, filed Jul. 24, 2018; Chakraborty et al.
Co-pending U.S. Appl. No. 16/043,308, filed Jul. 24, 2018; Chakraborty et al.
Office Action dated Oct. 9, 2018, received in co-pending U.S. Appl. No. 16/043,308.

(Continued)

*Primary Examiner* — Yevgeny Valenrod
*Assistant Examiner* — Blaine G Doletski
(74) *Attorney, Agent, or Firm* — Matthew W. Smith

(57) ABSTRACT

Disclosed is a process for recovering formic acid from a formate ester that allows for recovery of a formic acid product comprising greater than 75 wt. % formic acid. Disclosed is also a process for producing formic acid by carbonylating a carrier alcohol, hydrolyzing the formate ester of the carrier alcohol, and recovering a formic acid product comprising greater than 70 wt. % formic acid. Discloses are carrier alcohols that enable more favorable hydrolysis equilibriums and/or distillation sequences.

20 Claims, 2 Drawing Sheets

(56) References Cited

U.S. PATENT DOCUMENTS

| | | | |
|---|---|---|---|
| 8,455,677 | B2 | 6/2013 | Nakamura et al. |
| 8,969,632 | B2 | 3/2015 | Norman et al. |
| 9,040,748 | B2 | 5/2015 | Janka et al. |
| 9,493,395 | B2 | 11/2016 | Janka et al. |
| 2015/0151289 | A1 | 6/2015 | Mikhailine et al. |
| 2015/0274621 | A1 | 10/2015 | Fairweather et al. |
| 2016/0318956 | A1 | 11/2016 | Quintaine et al. |
| 2016/0326202 | A1 | 11/2016 | Morris et al. |

FOREIGN PATENT DOCUMENTS

| | | |
|---|---|---|
| GB | 2 166 522 A | 9/1983 |
| WO | WO 82/03854 A1 | 11/1982 |
| WO | WO 2006/106483 A1 | 10/2006 |
| WO | WO 2006/106484 A1 | 10/2006 |
| WO | WO 2013/079659 A1 | 6/2013 |
| WO | WO 2015/091158 A1 | 6/2015 |
| WO | WO 2017/194663 A1 | 11/2017 |

OTHER PUBLICATIONS

Co-pending U.S. Appl. No. 16/043,312, filed Jul. 24, 2018; Chakraborty et al.
Co-pending U.S. Appl. No. 16/043,317, filed Jul. 24, 2018; Chakraborty et al.
Notice of Allowance dated Nov. 15, 2018 received in U.S. Appl. No. 16/043,317.
Co-pending U.S. Appl. No. 16/043,320, filed Jul. 24, 2018; Chakraborty et al.
Notice of Allowance dated Nov. 2, 2018 received in U.S. Appl. No. 16/043,320.
Notice of Allowance dated Nov. 15, 2018 received in U.S. Appl. No. 16/043,320.
Co-pending U.S. Appl. No. 16/043,324, filed Jul. 24, 2018; Barnicki et al.
Wittstock et al.; "Nanoporous Gold Catalysts for Selective Gas-Phase Oxidative Coupling of Methanol at Low Temperature;" Science; 2010; vol. 327; pp. 319-323.
Wang et al.; "Graphene-supported Au—Pd bimetallic nanoparticles with excellent catalytic performance in selective oxidation of methanol to methyl formate;" Chem. Commun., 2013, 49, pp. 8250-8252.
Liu et al.; "Methanol Selective Oxidation to Methyl Formate over $ReO_x/CeO_2$ Catalysts;" Catal. Lett.; 2008; 120; pp. 274-280.
Huang et al.; "Effect of treatment temperature on structures and properties of zirconia-supported ruthenium oxide catalysts for selective oxidation of methanol to methyl formate;" Catalysis Today; 2012; 183; pp. 58-64.
Kaichev et al.; "Selective oxidation of methanol to form dimethoxymethane and methyl formate over a monolayer $V_2O_5/TiO_2$ catalyst;" Journal of Catalysis; 2014; 311; pp. 59-70.
Itagaki et al.; "Transition Metal Homogeneous Catalysis for Liquid-Phase Dehydrogenation of Methanol;" Journal of Molecular Catalysis; 1987; 41; pp. 209-220.
Smith et al.; "The Ruthenium-Catalysed Conversion of Methanol into Methyl Formate;" Journal of Organometallic Chemistry; 1985; 291; pp. C13-C14.
Yang et al.; "Mechanistic study on dehydrogenation of methanol with $[RuCl_2(PR_3)_3]$-type catalyst in homogeneous solutions;" Journal of Molecular Catalysis A: Chemical; 1996; 108; pp. 87-93.
Yamakawa et al.; "Catalytic Reaction of Methanol with a Series of Ruthenium (II) Complexes and the Mechanism of the Formation of Acetic Acid from Methanol Alone;" J. Chem. Soc. Dalton Trans.; 1994; pp. 2265-2269.
Shinoda et al.; "One-step Formation of Methyl Acetate with Methanol used as the Sole Source and Catalysis by Ru"-Sn" Cluster Complexes;" J. Chem. Soc., Chem. Commun.; 1990; pp. 1511-1512.
Kuriyama et al.; "Catalytic Hydrogenation of Esters. Development of an Efficient Catalyst and Processes for Synthesising (R)-1,2-Propanediol and 2-(I-Menthoxy)ethanol;" Org. ProcessRes. Dev.; 2012; 16; pp. 166-171.
Liu et al.; "Towards a Sustainable Synthesis of Formate Salts: Combined Catalytic Methanol Dehydrogenation and Bicarbonate Hydrogenation;" Angew. Chem. Int. Ed.; 2014; 53; pp. 7085-7088.
Alberico et al.; "Selective Hydrogen Production from Methanol with a Defined Iron Pincer Catalyst under Mild Conditions;" Angew. Chem. Int. Ed.; 2013; 52; pp. 14162-14166.
Werkmeister et al.; "Pincer-Type Complexes for Catalytic (De)Hydrogenation and Transfer (De)Hydrogenation Reactions: Recent Progress;" Chem. Eur. J.; 2015; 21; pp. 12226-12250.
Chakraborty et al.; "Nickel and Iron Pincer Complexes as Catalysts for the Reduction of Carbonyl Compounds;" Acc. Chem. Res.; 2015; 48; pp. 1995-2003.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; Structure of "$\kappa^4$-$Ph_4C_4CO$)($CO$)$_3$Ru—a Catalyst Precursor in H-Transfer and Dehydrogenation Reactions of Alcohols;" Inorganica Chimica Acta; 1985; 97; pp. L25-L26.
Warner et al.; "Shvo's Catalyst in Hydrogen Transfer Reactions;" Top Organomet Chem; 2011; 37; pp. 85-125.
Zhang et al.; "Facile Conversion of Alcohols into Esters and Dihydrogen Catalyzed by New Ruthenium Complexes;" J. Am. Chem. Soc.; 2005; 127; pp. 10840-10841.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.
Chakraborty et al.; "A Molecular Iron Catalyst for the Acceptorless Dehydrogenation and Hydrogenation of N-Heterocycles;" J. Am. Chem. Soc.; 2014; 136; pp. 8564-8567.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Chakraborty et al.; "Iron-Based Catalysts for the Hydrogenation of Esters to Alcohols;" J. Am. Chem. Soc.; 2014; 136; pp. 7869-7872.
Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.
Hu et al.; "Rechargeable Hydrogen Storage System Based on the Dehydrogenative Coupling of Ethylenediamine with Ethanol;" Angew. Chem. Int. Ed.; 2016; 55; pp. 1061-1064.
Kim et al.; "Ruthenium-Catalyzed Urea Synthesis Using Methanol as the C1 Source;" Org. Lett.; 2016; 18; pp. 212-215.
Crabtree, Robert H.; "Resolving Heterogeneity Problems and Impurity Artifacts in Operationally Homogeneous Transition Metal Catalysts;" Chem. Rev.; 2012; 112; pp. 1536-1554.
Gnanadesikan et al.; "Direct Catalytic Asymmetric Aldol-Tishchenko Reaction;" J. Am. Chem. Soc.; 2004; 126; pp. 7782-7783.
Haslam, Edwin; "Tetrahedron Report No. 93—Recent Developments in Methods for the Esterification and Protection of the Carboxyl Group;" Tetrahedron; 1980; vol. 36; pp. 2409-2433.
Gregory et al.; "The Production of Ethyl Acetate From Ethylene and Acetic Acid Using Clay Catalysts;" Clay Minerals; 1983; 18; pp. 431-435.
Goldemberg, José; "Ethanol for a Sustainable Energy Future;" Science; 2007; vol. 315; pp. 808-810.
Wang et al.; "Direct transformation of ethanol to ethyl acetate on Cu/ZrO2 catalyst;" Reac. Kinet. Mech. Cat.; 2010; 101; pp. 365-375.
Inui et al.; "Effective formation of ethyl acetate from ethanol over Cu—Zn—Zr—Al—O catalyst;" Journarl of Molecular Catalysis A: Chemical; 2004; 216; pp. 147-156.
Zonetti et al.; "Chemicals from ethanol—The dehydrogenative route of the ethyl acetate one-pot synthesis;" Journal of Molecular Catalysis A: Chemical; 2011; 334; pp. 29-34.
Medeiros et al.; "The role of water in ethanol oxidation over SnO2-supported molybdenum oxides;" Catalysis Letters; 69; 2000; pp. 79-82.

(56) References Cited

OTHER PUBLICATIONS

Gunanathan et al.; "Applications of Acceptorless Dehydrogenation and Related Transformations in Chemical Synthesis;" Science; 2013; vol. 341; pp. 249.
Bertoli et al.; "Osmium and Ruthenium Catalysts for Dehydrogenation of Alcohols;" Organometallics; 2011; 30; pp. 3479-3482.
Nielsen et al.; "Efficient Hydrogen Production from Alcohols under Mild Reaction Conditions;" Angew. Chem. Int. Ed.; 2011; 50; pp. 9593-9597.
Morton et al.; "Molecular Hydrogen Complexes in Catalysis: Highly Efficient Hydrogen Production from Alcoholic Substrates catalyzed by Ruthenium Complexes;" J. Chem. Soc., Chem. Commun.; 1988; pp. 1154-1156.
Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.
Carlini et al.; "Selective synthesis of isobutanol by means of the Guerbet reaction Part 2. Reaction of methanol/ethanol and methanol/ethanol/n-propanol mixtures over copper based/MeONa catalytic systems;" Journal of Molecular Catalysis A: Chemical; 200; 2003; pp. 137-146.
Furukawa et al.; "High Polymerization of Acetaldehyde by Alumina—A New Method of Preparation of Polyether;" Journal of Polymer Science; vol. XXXVI; Issue No. 130; 1959; pp. 546.
Degering et al.; "Polymerization of Acetaldehyde and Crotonaldehyde Catalyzed by Aliphatic Tertiary Amines;" Journal of Polymer Science; vol. VII; No. 6; pp. 653-656.
Teunissen et al.; "Ruthenium catalyzed hydrogenation of dimethyl oxalate to ethylene glycol;" Chem. Commun.; 1997; pp. 667-668.
Zhang et al.; "Efficient Homogeneous Catalytic Hydrogenation of Esters to Alcohols;" Angew. Chem. Int. Ed.; 2006; 45; pp. 1113-1115.
Saudan et al.; "Dihydrogen Reduction of Carboxylic Esters to Alcohols under the Catalysis of Homogeneous Ruthenium Complexes: High Efficiency and Unprecedented Chemoselectivity;" Angew. Chem. Int. Ed.; 2007; 46; pp. 7473-7476.
Dub et al.; "Catalytic Reductive Transformations of Carboxylic and Carbonic Acid Derivatives Using Molecular Hydrogen;" ACS Catal.; 2012; 2; pp. 1718-1741.
Clarke, Matthew L.; "Recent developments in the homogeneous hydrogenation of carboxylic acid esters;" Catal. Sci. Technol.; 2012; 2; pp. 2418-2423.
Chakraborty et al.; "First-row transition metal catalyzed reduction of carbonyl functionalities: a mechanistic perspective;" Dalton Trans.; 2010; 39; pp. 7427-7436.
Zell et al.; "Unprecedented Iron-Catalyzed Ester Hydrogenation. Mild, Selective, and Efficient Hydrogenation of Trifluoroacetic Esters to Alcohols Catalyzed by an Iron Pincer Complex;" Angew. Chem. Int. Ed.; 2014; 53; pp. 4685-4689.
Werkmeister et al.; "Hydrogenation of Esters to Alcohols with a Well-Defined Iron Complex;" Angew. Chem. Int. Ed.; 2014; 53; pp. 8722-8726.
Wang et al.; "The Golden Age of Transfer Hydrogenation;" Chem. Rev.; 2015; 115; pp. 6621-6686.
Lee et al.; "Transfer Hydrogenation of Ketones, Nitriles, and Esters Catalyzed by a Half-Sandwich Complex of Ruthenium;" ChemCatChem; 2015; 7; pp. 107-113.
Dubey et al.; "Catalytic Ester Metathesis Reaction and Its Application to Transfer Hydrogenation of Esters;" ACS Catal.; 2016/ 6; pp. 3998-4002.
Dusselier et al.; "Lactic acid as a platform chemical in the biobased economy: the role of chemocatalysis;" Energy Environ. Sci.; 2013; 6; pp. 1415-1442.
Carnahan et al.; "Ruthenium-catalyzed Hydrogenation of Acids to Alcohols;" Journal of the American Chemical Society; 1955; vol. 77; Issue 14; pp. 3766-3768.
Matteoli et al.; "Structure and catalytic activity of phosphine-substituted ruthenium carbonyl carboxylates;" Journal of Organometallic Chemistry; 498; 1995; pp. 177-186.

https://www.ube-ind.co.jp/ube/en/news/2015/20160316_01.html Ube Industries Licenses DMC Technology and Agrees to Establish Joint Venture for High-Purity DMC, 3 pages.
Vom Stein et al.; "Highly Versatile Catalytic Hydrogenation of Carboxylic and Carbonic Acid Derivatives using a Ru-Triphos Complex: Molecular Control over Selectivity and Substrate Scope;" J. Am. Chem. Soc.; 2014; 136; pp. 13217-13225.
Shuklov et al.; "Propane-1,2-diols from Dilactides, Oligolactides, or Poly-L-Lactic Acid (PLLA): From Plastic Waste to Chiral Bulk Chemicals;" Chem. Eur. J.; 2014; 20; pp. 957-960.
Spasyuk et al.; "Acceptorless Dehydrogenative Coupling of Ethanol and Hydrogenation of Esters and Imines;" Organometallics; 2012; 31; pp. 5239-5242.
Fan et al.; "Efficient Hydrogenation of Ethyl Lactate to 1,2-Propanediol over Ru-B/TiO$_2$ in Aqueous Solution;" Chemistry Letters; vol. 37, No. 8; 2008; pp. 852-853.
Zhang et al.; "Aqueous-phase hydrogenation of lactic acid to propylene glycol;" Applied Catalysis A: General; 2001; 219; pp. 89-98.
Adkins et al.; "The Hydrogenation of Esters to Alcohols at 25-150°;" Journal of the American Chemical Society; 1948; vol. 70; Issue 9; pp. 3121-3125.
Broadbent et al.; "Rhenium and Its Compounds as Hydrogenation Catalysts. III. Rhenium Heptoxide;" Journal of Organic Chemistry; 1959; vol. 24; Issue 12; pp. 1847-1854.
Hietala et al.; "Formic Acid"; Ullmann's Encyclopedia of Industrial Chemistry; vol. 16; 2012; Wiley-VCH Verlag GmbH & Co. KGaA, Weinheim; pp. 13-33.
Di Girolamo et al.; "Acidic and basic ion exchange resins for industrial applications;" Journal of Molecular Catalysis A: Chemical; 2001; 177; pp. 33-40.
Nørskov et al.; "Towards the computational design of solid catalysts;" Nature Chemistry; vol. 1; Apr. 2009; pp. 37-46.
Bielinski et al.; "Base-Free Methanol Dehydrogenation Using a Pincer-Supported Iron Compound and Lewis Acid Co-catalyst;" ACS Catal.; 2015; 5; pp. 2404-2415.
Fairweather et al.; "Homogeneous Hydrogenation of Fatty Acid Methyl Esters and Natural Oils under Neat Conditions;" Organometallics; 2015; 34; pp. 335-339.
Qu et al.; "Computational Mechanistic Study of Fe-Catalyzed Hydrogenation of Esters to Alcohols: Improving Catalysis by Accelerating Precatalyst Activation with a Lewis Base;" ACS Catal.; 2014; 4; pp. 4377-4388.
Notification of Transmittal of the International Search Report and the Written Opinion of the International Searching Authority dated Oct. 19, 2018 for International Application No. PCT/US2018/044482.
Notification of Transmittal of the International Search Report and the Written Opinion of the International Searching Authority dated Oct. 19, 2018 for International Application No. PCT/US2018/044485.
Monnereau et al.; "Efficient Synthesis of Differentiated syn-1,2-Diol Derivatives by Asymmetric Transfer Hydrogenation-Dynamic Kinetic Resolution of α-Alkoxy-Substituted β-Ketoesters;" Chemistry—A European Journal; 2015; 21; pp. 11799-11806.
Kim et al.; "Transfer Hydrogenation of Organic Formates and Cyclic Carbonates: An Alternative Route to Methanol from Carbon Dioxide;" ACS Catal.; 2014; 4; pp. 3630-3636.
Patil et al.; "Immobilized Iron Metal-Containing Ionic Liquid-Catalyzed Chemoselective Transfer Hydrogenation of Nitroarenes into Anilines;" ACS Sustainable Chem. Eng.; 2016; 4; pp. 429-436.
Notification of Transmittal of the International Search Report and the Written Opinion of the International Searching Authority dated Oct. 19, 2018 for International Application No. PCT/US2018/044476.
Notification of Transmittal of the International Search Report and the Written Opinion of the International Searching Authority dated Oct. 26, 2018 for International Application No. PCT/US2018/044518.
Pandey et al.; "Acceptorless Alcohol Dehydrogenation: A Mechanistic Perspective;" Proc. Natl. Acad. Sci., India, Sect. A Phys. Sci.; 2016; vol. 86; Issue 4; pp. 561-579.

(56) References Cited

OTHER PUBLICATIONS

Notification of Transmittal of the International Search Report and the Written Opinion of the International Searching Authority dated Oct. 26, 2018 for International Application No. PCT/US2018/044512.

Iranpoor et al.; "Silphos [$PCl_{3-n}(SiO_2)_n$]: a heterogeneous phosphine reagent for formylation and acetylation of alcohols and amines with ethyl formate and acetate;" Tetrahedron Letters; 46; 2005; pp. 7963-7966.

Lane et al.; "Iron-Catalyzed Amide Formation from the Dehydrogenative Coupling of Alcohols and Secondary Amines;" Organometallics; 2017; 36; pp. 2020-2025.

Notification of Transmittal of the International Search Report and the Written Opinion of the International Searching Authority dated Oct. 26, 2018 for International Application No. PCT/US2018/044506.

Notification of Transmittal of the International Search Report and the Written Opinion of the International Searching Authority dated Nov. 6, 2018 for International Application No. PCT/US2018/044521.

Notice of Allowance dated Oct. 21, 2019 received in U.S. Appl. No. 16/043,324.

* cited by examiner

PROCESS FOR MAKING FORMIC ACID UTILIZING HIGHER-BOILING FORMATE ESTERS

CROSS REFERENCE TO RELATED APPLICATION

This application claims the benefit of Provisional Application 62/540,343 filed on Aug. 2, 2017 under 35 U.S.C. § 119(e)(1), the entire content of which is incorporated herein by reference.

TECHNICAL FIELD

This invention pertains to the recovery of formic acid from a formate ester mixture, wherein the formate ester mixture is hydrolyzed to produce formic acid and a carrier alcohol. More particularly, this invention pertains to a process for recovery of formic acid wherein concentrated formic acid can be recovered directly from the hydrolysis effluent. When utilized within a formate synthesis process, such as carbonylation or dehydrogenative coupling of methanol with an alcohol, for producing formic acid, improved energy efficiency can be obtained versus the traditional carbonylation of methanol to methyl formate.

BACKGROUND

The synthesis of formic acid from either carbon monoxide and water or carbon dioxide and hydrogen is thermodynamically highly unfavorable and is not a practiced industrial approach to formic acid synthesis. In an effort to overcome these limitations, formic acid has been produced industrially by a number of indirect methods, requiring complicated multi-step reaction and separation sequences, with high capital and energy costs (Reutemann, W.; Kieczka, H., "Formic Acid", in Ullmann's Encyclopedia of Industrial Chemistry, Volume 16, 2012, Wiley-VCH Verlag GmbH & Co. KGaA, Weinheim, pp. 13-33). One such method is the acidification of formate salts, produced for example, as a by-product of the Cannizzaro reaction for the production of formaldehyde/aldehyde-based polyols such as trimethylolpropane. This method results in the generation of a salt such as sodium sulfate, with corresponding disposal issues.

The production of formic acid by hydrolysis of formamide, formed by a three-step process involving carbonylation of methanol to methyl formate, reaction with ammonia to produce formamide, followed by hydrolysis-salt formation, is another commercial approach to formic acid synthesis. However, the consumption of ammonia and sulfuric acid, along with the unavoidable production of ammonium sulfate, have made this process economically inferior.

The predominant industrial process for the production of formic acid is via base-catalyzed carbonylation of methanol to methyl formate, followed by hydrolysis of methyl formate to methanol and formic acid, and subsequent separation of water, methanol, and unreacted methyl formate from liberated free formic acid. This process suffers from many drawbacks. Although readily carbonylated, methanol conversion is relatively low (typically less than 30%) at economically viable CO pressures. Methyl formate must be distilled from unconverted methanol and the active base catalyst without reversion of the formate back to CO and methanol. The hydrolysis of methyl formate is thermodynamically unfavorable, resulting in only 25-30% conversion, even at a molar ratio of water/ester of 2/1 or higher. If conventional distillation is used to process the hydrolysis reactor effluent, all of the unreacted methyl formate and by-product methanol must be distilled overhead, since formic acid is higher boiling than methyl formate and methanol. The low conversion leads to high recycle ratios of unreacted methyl formate to produced formic acid (typically 3-4 tons of recycled methyl formate per ton of formic acid produced).

Distillation of a hydrolysis reactor effluent (with methanol and methyl formate taken overhead) also produces an underflow that is relatively dilute formic acid in water (typically less than 40 wt. % formic acid), and since formic acid and water form a maximum-boiling azeotrope, the separation of formic acid from water is a relatively energy and capital intensive endeavor. The conventional approach to formic acid-water separation is pressure-swing distillation, whereas the composition of the water/formic acid azeotrope varies fairly significantly with pressure. For example, the water/formic acid wt./wt. ratio is about 42/58 at 0.04 bara, 40/60 at 0.067 bara, 25/75 at 1.013 bara, 20/80 at 2.03 bara, 17/83 at 3.04 bara, and 16/84 at 4.05 bara. In the pressure swing distillation system, water is distilled overhead in a first high pressure column, and the maximum boiling formic acid-water azeotrope is taken as a bottoms product. The azeotrope is then further distilled in a second low pressure column with typically 90-99% formic acid as distillate, and a new maximum-boiling azeotrope composition taken as underflow, which is recycled to the high-pressure column. Thus, all the water entering the two-column system with the feed eventually exits as part of the distillate in the high-pressure column. Although the distillate from the high-pressure column can be used for heat integration purposes (either to generate steam upon condensing or directly as a condensing heat source), this pressure swing distillation is very energy intensive, requiring typically 3 to 5 tons of steam per ton of formic acid produced as high purity formic acid.

Several methods have been proposed to improve both the hydrolysis conversion of methyl formate to formic acid and methanol and the separation of formic acid-water. Extraction processes have been proposed for improving the energy consumption for separating formic acid and water, as for example using secondary amides (Hohenschutz et al., U.S. Pat. No. 4,217,460, Aug. 12, 1980, and Wolf et al., U.S. Pat. No. 4,326,073, Apr. 20, 1982). These processes introduce new contaminants into the system and require relatively high vacuum distillation and high energy consumption to separate formic acid from the extractant. Hohenschutz et al., proposed adding a tertiary nitrogen base (U.S. Pat. No. 4,218,568, Aug. 19, 1980) or weak base formamide derivative (U.S. Pat. No. 5,206,433, Apr. 27, 1993) directly to the hydrolysis reaction mixture to shift the equilibrium conversion by forming a salt of the base and formic acid. Such methods also require considerable energy to decompose the salt and liberate formic acid. Buelow et al (U.S. Pat. No. 4,076,594, Feb. 28, 1978) discloses the use of basic extractive distillation agents for separation of formic acid and water, but water must still be distilled overhead and the base-formic acid complex decomposed, resulting again in high energy usage.

Conventional carbonylation-hydrolysis processes utilizing methanol as the carrier alcohol and distillative separation techniques or processes utilizing basic extractants, reactants, or extractive distillation agents are capital and energy intensive. Thus, there is a need for lower energy process for synthesis of formic acid which overcomes these deficiencies.

BRIEF SUMMARY

In an embodiment, a process for recovering formic acid from a formate ester mixture comprises feeding the formate ester mixture and water to a hydrolysis zone. The formate ester mixture comprises a formate ester of a carrier alcohol and the carrier alcohol. The process comprises hydrolyzing the formate ester mixture in the hydrolysis zone to produce a hydrolysis effluent comprising the formate ester of the carrier alcohol, formic acid, and the carrier alcohol. The process also comprises feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

In another embodiment, a process for producing formic acid comprises a) feeding carbon monoxide, a fresh feed, and a catalyst feed to a carbonylation zone. The fresh feed comprises a carrier alcohol. The process comprises carbonylating the carrier alcohol to produce a formate ester of the carrier alcohol and removing a carbonylation effluent. The carbonylation effluent comprises the formate ester of the carrier alcohol, the carrier alcohol and a homogeneous catalyst. The process comprises b) feeding the carbonylation effluent to a catalyst separation zone and removing a catalyst mixture and a formate ester mixture. The catalyst mixture comprises a homogeneous catalyst and the carrier alcohol, and the formate ester mixture comprises the formate ester of the carrier alcohol. The process comprises c) feeding the formate ester mixture and water to a hydrolysis zone, hydrolyzing the formate ester of the carrier alcohol, and removing a hydrolysis effluent. The hydrolysis effluent comprises the formate ester of the carrier alcohol, formic acid, and the carrier alcohol. The process also comprises d) feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

In yet another embodiment, a process for producing formic acid comprises a) feeding methanol, an alcohol feed, and a catalyst recycle to a dehydrogenative coupling (DHC) zone. The alcohol feed comprises a carrier alcohol and less than 1 wt. % water. The process comprises performing a DHC reaction of methanol with the carrier alcohol to produce a formate ester of the carrier alcohol, and removing a DHC effluent. The DHC effluent comprises the formate ester of the carrier alcohol and a homogeneous catalyst. The process comprises b) feeding the DHC effluent to a catalyst separation zone and removing the catalyst recycle and a formate ester mixture. The catalyst recycle comprises the homogeneous catalyst, and the formate ester mixture comprises the formate ester of the carrier alcohol. The process comprises c) feeding the formate ester mixture and water to a hydrolysis zone, hydrolyzing the formate ester of the carrier alcohol, and removing a hydrolysis effluent. The hydrolysis effluent comprises the formate ester of the carrier alcohol, formic acid, and the carrier alcohol. The process also comprises d) feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The carrier alcohol is selected from the group consisting of $C_5$ to $C_{14}$ secondary and tertiary alcohols. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

DETAILED DESCRIPTION

Figure 1:
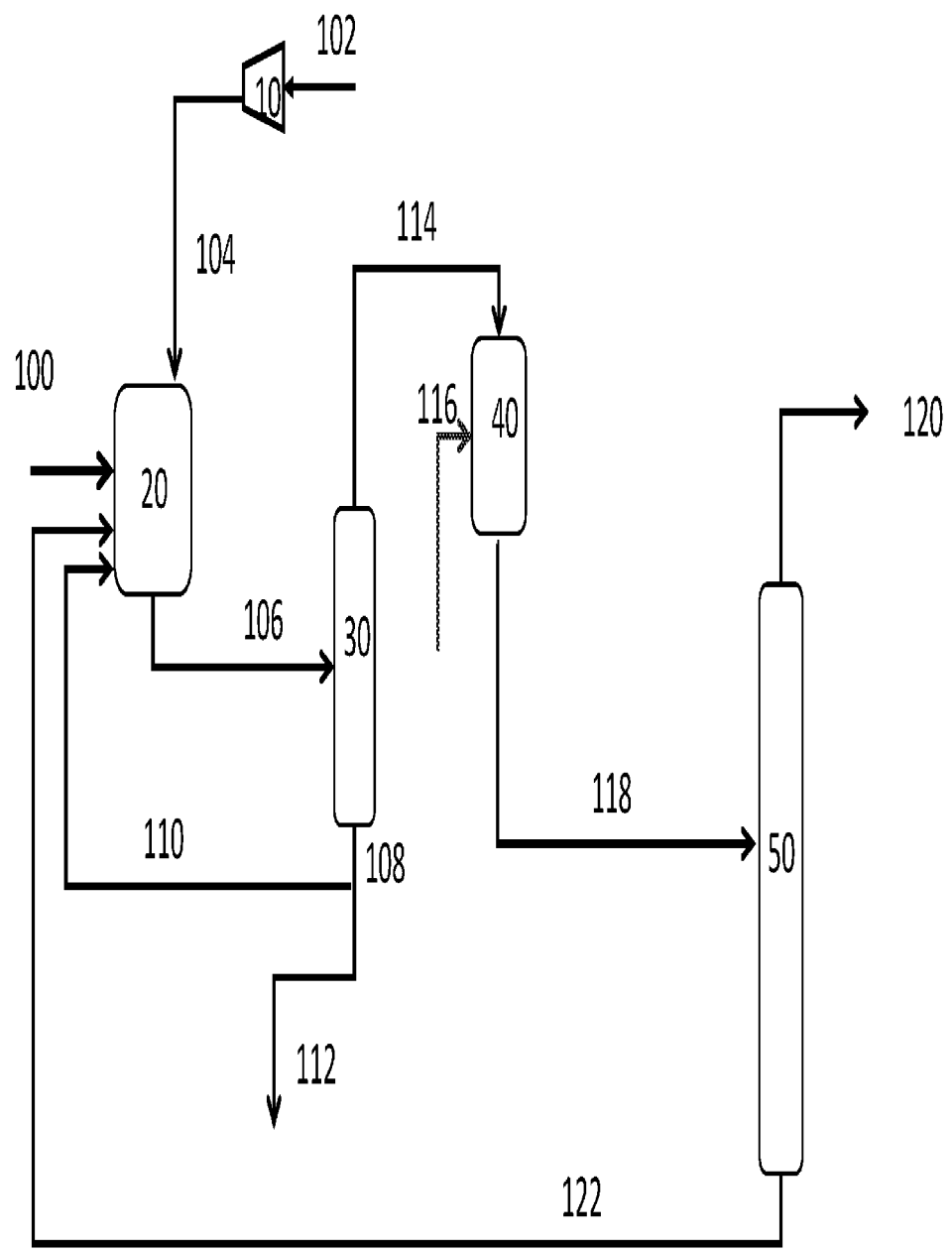
FIG. 1 illustrates a non-limiting process flow diagram of the production of formic acid via carbonylation of 1-propoxy-2-propanol.

In an embodiment, a process for recovering formic acid from a formate ester mixture comprises feeding the formate ester mixture and water to a hydrolysis zone. The formate ester mixture comprises a formate ester of a carrier alcohol and the carrier alcohol. The process comprises hydrolyzing the formate ester mixture in the hydrolysis zone to produce a hydrolysis effluent comprising the formate ester of the carrier alcohol, formic acid, and the carrier alcohol. The process also comprises feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

Unless otherwise indicated, all numbers expressing quantities of ingredients, properties such as molecular weight, reaction conditions, and so forth used in the specification and claims are to be understood as being modified in all instances by the term "about."

As used herein, the indefinite articles "a" and "an" mean one or more, unless the context clearly suggests otherwise.

Similarly, the singular form of nouns includes their plural form, and vice versa, unless the context clearly suggests otherwise.

It is to be understood that the mention of one or more process steps does not preclude the presence of additional process steps before or after the combined recited steps or intervening process steps between those steps expressly identified. It is also to be understood that the feeding of a process flow to a zone of the process or the removing of a process flow from the process includes the feeding or removing of a portion of the process flow and/or the entire process flow, unless otherwise indicated. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "boiling point temperature", as used herein, refers to the temperature of a substance at which the vapor pressure of the liquid equals the operating pressure and the liquid changes into a vapor. The terms, "higher boiling point temperature", "boiling point temperature higher than" or "compound A has a boiling point temperature higher than compound B", as used herein, refers to a substance being at a higher temperature before the vapor pressure of the liquid equals the operating temperature.

The term, "carbonylation zone", as used herein, refers to a part of a process wherein the "carrier alcohol" is carbonylated. The term, "carbonylating", as used herein refers the reaction of a carrier alcohol with carbon monoxide. The term, "carbonylation effluent", as used herein, refers to the effluent from the "carbonylation zone". The term, "catalyst separation zone", as used herein, may refer to a part of the process wherein the "homogeneous catalyst" is separated from the "carbonylation effluent". The term, "catalyst mixture', as used herein, refers to the stream leaving the "catalyst separation zone" which is rich in the "homogeneous catalyst". The "catalyst mixture" may be further processed and/or fed to the "carbonylation zone".

The term, "dehydrogenative coupling zone" or "DHC zone", as used herein, refers to a part of a process wherein a dehydrogenative couple reaction of methanol and the "carrier alcohol" is performed. The term, "dehydrogenative coupling effluent" or "DHC effluent", as used herein, refers to the effluent from the "DHC zone". The term, "catalyst separation zone", as used herein, may refer to a part of the process wherein the "homogeneous catalyst" is separated from the "DHC effluent". The term, "catalyst recycle", as used herein refers to the stream leaving the "catalyst separation zone" which is rich in the "homogenous catalyst" and recycled to the "DHC zone".

The term, "carrier alcohol", as used herein, refers to a compound comprising at least one OH group, at least 5 carbon atoms, and no more than 14 carbon atoms. Non-limiting examples of carrier alcohols include simple alcohols, polyols, polyol ethers, and polyol esters. A "secondary alcohol", as used herein, refers to a compound in which a hydroxyl group, —OH is attached to a saturated carbon atom which has two carbon atoms attached to it. A "tertiary alcohol", as used herein, refers to a compound in which a hydroxyl group, —OH, is attached to a saturated carbon atom which has three other carbon atoms attached to it. An "alcohol/ester stream", as used herein, refers to a process stream removed from the distillation zone which has less than 5 wt. % formic acid, may be low in water, and may be recycled to a "carbonylation zone" or a "DHC zone".

The "distillation zone" is the part of the process wherein the formic acid is distilled from the other components. In some aspects, the formate ester of a carrier alcohol undergoes further hydrolysis in the "distillation zone". The "distillation zone" comprises at least a first "distillation column". The term "distillation column", as used herein, refers to a multi-stage fractionation unit operation with reflux wherein the formic acid is separated from a mixture and the separation occurs across the multi-stage unit. The term "distillate", as used herein, refers to the stream leaving the top of the "distillation column" (often after having been liquefied in a condenser). The term "bottoms", as used herein, refers to the stream leaving the bottom or base of the "distillation column". The "base temperature" as used herein, refers to the temperature as measured at or near the bottom of a "distillation column", for example, at the base of the column, or of the "bottoms" as it leaves the "distillation column". The term "stages", as used herein, refers to a vapor-liquid contacting device where bubbles of vapor are distributed into a holding volume of boiling liquid. Liquid and vapor flow in counter-current directions. A "lower stage" of the "distillation column" is closer to the bottom and a "higher stage" is closer to the top.

The term, "formate ester", as used herein, refers to an ester for the formula (H—C—O—O—R). The term "formate ester of a carrier alcohol", as used herein, refers a formate ester (or formate esters) wherein the "carrier alcohol" is the product of hydrolysis of the formate ester(s). In other words, the reaction of the "formate ester of a carrier alcohol" with water produces an equilibrium mixture with formic acid and the "carrier alcohol". One skilled in the art will recognize that more than one formate ester of a carrier alcohol may exist when the carrier alcohol is a diol. For example, the formate ester of 1, 2propanediol include each of the monoformate and diformate configurations, 1-hydoxypopan-2-yl-formate, 2-hydroxypropyl formate, and propane-1,2-diyldiformate. It may also refer to the specific formate ester produced by the carbonylation of a carrier alcohol or the dehydrogenative coupling (DHC) of methanol with a carrier alcohol. The term, "formate ester mixture", as used herein, refers to a process stream comprising the "formate ester of the carrier alcohol" and may also comprise the "carrier alcohol".

The term, "formic acid product", as used herein, refers to a process stream(s) comprising the purified formic acid. Typically, commercial grades of formic acid comprise between 78 wt. % and 99 wt. % formic acid.

The term "fresh feed", as used herein, refers to a raw material input to the "carbonylation zone" or "DHC zone" that is new to the process, i.e., it is not a recycle stream. The term "catalyst feed", as used herein refers to the input of the homogeneous catalyst to the "carbonylation zone". The "catalyst feed" may or may not comprise catalyst recycled from the "catalyst separation zone".

The term, "homogeneous catalyst", as used herein refers to a catalyst that is soluble or partly soluble in the reaction mixture under reaction conditions. For a process comprising carbonylation, particularly useful catalysts include alkali metal alkoxides of the carrier alcohol. For processes comprising dehydrogenative coupling (DHC) of methanol with an alcohol, iron-based catalysts supported by pincer ligands are useful catalysts.

The "hydrolysis zone" is a part of the process wherein the formate ester mixture is hydrolyzed without a separation of components that would impact the equilibrium limited hydrolysis reaction. The term "hydrolyzing", as used herein, refers to the reaction of an ester with water. The term "hydrolysis reactor", as used herein, refers to the equipment wherein at least part of the hydrolysis reaction occurs. The term, "hydrolysis effluent", as used herein, refers to the effluent from the hydrolysis reaction zone and/or hydrolysis reactor.

The term, "maximum-boiling azeotrope", as used herein, refers to a mixture of at least two components whose proportions cannot be altered by simple distillation, wherein the boiling point of the mixture is higher than the boiling point of any of the components. The term, "minimum-boiling azeotrope", as used herein, refers to a mixture of at least two components whose proportions cannot be altered by simple distillation, wherein the boiling point of the mixture is lower than the boiling point of any of the components. The term, "azeotrope boiling point temperature", as used herein refers to the temperature at which a mixture of at least two components boils with the composition of the liquid and vaper being the same. Formic acid and water form a maximum-boiling azeotrope at temperatures and pressures of industrial interest. The term "formic acid in an amount within x weight percentage points of an amount of formic acid in a formic acid/water azeotrope", as used herein, refers to the weight percent formic acid/water azeotrope minus the weight percent of formic acid in a stream at the given conditions being within x percentage points. For example, if at the operating pressure of the distillation column, the formic acid/water azeotrope comprises 80 wt. % formic acid, and the bottoms comprises 84 wt. % formic acid, then the weight percent formic acid in the bottoms is within 4 percentage points (84-80) of the azeotrope. When approaching the azeotrope from the other direction, if at the operating pressure of the distillation column, the formic acid/water azeotrope comprises 80 wt. % formic acid, and the bottoms comprises 75 wt. % formic acid, then the weight percent formic acid in the bottoms is within 5 percentage points (80-75) of the azeotrope.

The term, "molar ratio", as used herein, refers to the moles of one component divided by the moles of another component. For example, if the molar ratio of water to 1-ethoxy-2-propyl formate is 2:1, then for every mole of 1-ethoxy-2-propyl formate there are 2 moles of water.

The term, "n-component", as used herein, refers to the number of different types of chemical compounds involved. For example, a 3-component mixture has three chemical compounds. A 2-component azeotrope is an azeotrope formed by a mixture of two chemical compounds.

The term, "operating pressure" as used herein, refers to the pressure or pressure range of a zone or a piece of equipment when processing step, such as a reaction or a separation, occurs. The "operating pressure" of a distillation column refers to the pressure as measured at or near the top of the distillation column, for example, at the condenser or at the vacuum pump.

The term, "overall conversion", as used herein, refers to the moles of formic acid in the formic acid product leaving the process from the distillation zone divided by the sum of the moles of formic acid and formate ester of the alcohol in the formate ester mixture, multiplied by 100. The term "hydrolysis conversion", as used herein, refers to the moles of formic acid in the hydrolysis effluent divided by the sum of the moles of formic acid and formate ester of the alcohol in the formate ester mixture, multiplied by 100. The term, "distillation conversion", as used herein, refers the moles of formic acid in the formic acid product leaving the distillation zone divided by the sum of the moles of formic acid and formate ester of the carrier alcohol in the hydrolysis effluent, multiplied by 100. The term "overall conversion is x to y percentage points higher than hydrolysis conversion", as used herein means that the overall conversion minus the hydrolysis conversion is x to y. For example, if the overall conversion is 80% and it is 20 to 30 percentage points higher than the hydrolysis conversion, then the hydrolysis conversion is 50% to 60%.

In the present embodiment, a process for recovering formic acid from a formate ester mixture comprises feeding the formate ester mixture and water to a hydrolysis zone. The formate ester mixture comprises a formate ester of a carrier alcohol and the carrier alcohol. The carrier alcohol and formic acid are produced when the formate ester of the carrier alcohol is hydrolyzed.

The process by which the formate ester of the carrier alcohol is made is not particularly limited. In one aspect, the formate ester of the carrier alcohol is produced by the carbonylation of the carrier alcohol. In another aspect, the formate ester of the carrier alcohol is produced by Baeyer-Villinger oxidation of an aldehyde (e.g., oxidation of isobutyraldehyde to produce isopropyl formate). In another aspect, the formate ester of the carrier alcohol is produced by transesterification of methyl formate with the carrier alcohol. In yet another aspect, the formate ester is produced by the dehydrogenative coupling (DHC or dehydrocoupling) reaction of methanol with a secondary or tertiary alcohol.

In one aspect, the carrier alcohol is a compound consisting of at least one OH group and 5 to 14 carbon atoms. In other examples, the carrier alcohol consists of at least one OH group and 5 to 12 carbon atoms or 5 to 10 carbon atoms. The carrier alcohol has a higher boiling point temperature than a boiling point temperature of the formic acid/water azeotrope at the operating pressure of the first distillation column.

Non-limiting examples of favorable formate esters of the carrier alcohols for the present invention are formate ester of ethylene glycol, formate ester of 1,2-propanediol, formate ester of 1,3-propanediol, formate ester of 1,2-butanediol, formate ester of 1,3-butanediol, formate ester of 2,3-butanediol, formate ester of 1,4-butanediol, formate ester of 1,2-cyclohexanediol, formate ester of 1,3-cyclohexanediol, formate ester of 1,4-cyclohexanediol, formate ester of 1,2-phenylenedimethanol, formate ester of 1,3-phenylenedimethanol, formate ester of 1,4-phenylenedimethanol, formate ester of 1,2-cyclohexanedimethanol, formate ester of 1,3-cyclohexanedimethanol, formate ester of 1,4-cyclohexanedimethanol, formate ester of 2,2,4-trimethylpentane-1,3-diol; formate ester of $C_3$ to $C_8$ triols and polyols, such as formate ester of glycerol, formate ester of trimethylolethane, formate ester of trimethylolpropane, formate ester of trimethylolbutane; formate ester of glycol ethers, such as formate ester of diethylene glycol, formate ester of triethylene glycol, and formate ester of di and tri oligomers of propanediols and butanediols; and formate ester of $C_1$ to $C_6$ alkoxy ethers of diols, formate ester of glycol ethers, formate ester of triols and formate ester of polyols, such as formate ester of diethylene glycol monomethyl ether, formate ester of diethylene glycol monoethyl ether, formate ester of diethylene glycol monopropyl ether, formate ester of diethylene glycol monobutyl ether, formate ester of 1-ethoxy-2-propanol, formate ester of 1-propoxy-2-propanol, formate ester of 1-butoxy-2-propanol, formate ester of 2-ethoxy-1-propanol, formate ester of 2-propoxy-1-propanol, and formate ester of 2-butoxy-1-propanol.

In one aspect, formate ester of the carrier alcohol contains secondary alcohol groups, such as formate ester of 1-ethoxy-2-propanol, formate ester of 1-propoxy-2-propanol, formate ester of 1-butoxy-2-propanol, and formate ester of monoformate esters of diols with unexpectedly high hydrolysis equilibrium molar ratios for hydrolysis of the diformate ester, such as formate ester of ethylene glycol monoformate, formate ester of diethylene glycol monoformate, formate ester of 2-hydroxy-propylformate. In one aspect, the formate ester of carrier alcohol is selected from the group consisting of formate ester of [2,2,2]-bicyclo-1,4-octanediol, formate ester of adamantane-1,3,5,7-tetraol, and formate ester of adamantane-1,3-diol.

In one aspect, the formate ester of the carrier alcohol is selected from the group consisting of formate ester of ethylene glycol; formate ester of 1,2-propanediol; formate ester of 1,3-propanediol; formate ester of 1,2-butanediol; formate ester of 1,3-butanediol; formate ester of 2,3-butanediol; formate ester of 1,4-butanediol; formate ester of 1,2-cyclohexanediol; formate ester of 1,3-cyclohexanediol; formate ester of 1,4-cyclohexanediol; formate ester of 1,2-phenylenedimethanol; formate ester of 1,3-phenylenedimethanol; formate ester of 1,4-phenylenedimethanol; formate ester of 1,2-cyclohexanedimethanol; formate ester of 1,3-cyclohexanedimethanol; formate ester of 1,4-cyclohexanedimethanol; formate ester of 2,2,4-trimethylpentane-1,3-diol; formate ester of glycerol; formate ester of trimethylolethane; formate ester of trimethylolpropane; formate ester of trimethylolbutane; formate ester of diethylene glycol; formate ester of triethylene glycol; formate ester of di and tri oligomers of propanediols and butanediols; formate ester of diethylene glycol monomethyl ether; formate ester of diethylene glycol monoethyl ether; formate ester of diethylene glycol monopropyl ether; formate ester of diethylene glycol monobutyl ether; formate ester of 1-ethoxy-2-propanol; formate ester of 1-propoxy-2-propanol; formate ester of 1-butoxy-2-propanol; formate ester of 2-ethoxy-1-propanol; formate ester of 2-propoxy-1-propanol; formate ester of 2-butoxy-1-propanol; formate ester of ethylene glycol monoformate; formate ester of diethylene glycol monoformate; and formate ester of 2-hydroxy-propylformate. In one aspect, the formate ester of the carrier alcohol is selected from the group consisting of formate ester of ethylene glycol; formate ester of 1,2-propanediol; formate ester of 1,3-propanediol; formate ester of 1,2-butanediol; formate ester of 1,3-butanediol; formate ester of 2,3-butanediol; formate ester of 1,4-butanediol; formate ester of 1,2-cyclohexanediol; formate ester of 1,3-cyclohexanediol; formate ester of 1,4-cyclohexanediol; formate ester of 1,2-phenylenedimethanol; formate ester of 1,3-phenylenedimethanol; formate ester of 1,4-phenylenedimethanol; formate ester of 1,2-cyclohexanedimethanol; formate ester of 1,3-cyclohexanedimethanol; formate ester of 1,4-cyclohexanedimethanol; and formate ester of 2,2,4-trimethylpentane-1,3-diol. In one aspect, the carrier alcohol is selected from the group consisting of formate ester of glycerol; formate ester of trimethylolethane; formate ester of trimethylolpropane; formate ester of trimethylolbutane; formate ester of diethylene glycol; formate ester of triethylene glycol; and formate ester of di and tri oligomers of propanediols and butanediols. In one aspect, the carrier alcohol is selected from the group consisting of formate ester of diethylene glycol monomethyl ether; formate ester of diethylene glycol monoethyl ether; formate ester of diethylene glycol monopropyl ether; formate ester of diethylene glycol monobutyl ether; formate ester of 1-ethoxy-2-propanol; formate ester of 1-propoxy-2-propanol; formate ester of 1-butoxy-2-propanol; formate ester of 2-ethoxy-1-propanol; formate ester of 2-propoxy-1-propanol; and formate ester of 2-butoxy-1-propanol.

In one aspect, the formate ester of the carrier alcohol is selected from the group consisting of formate ester of ethylene glycol; formate ester of diethylene glycol; formate ester of diethylene glycol monomethyl ether; formate ester of 1,2-propane diol; formate ester of 1-propoxy-2-propanol; formate ester of 2-hydroxy-propanol; formate ester of 1-ethoxy-2propanol; and formate ester of 1-butoxy-2-propanol. In one aspect, the carrier alcohol is selected from the group consisting of formate ester of ethylene glycol, formate ester of diethylene glycol monomethyl ether, formate ester of diethylene glycol, and formate ester of 1-propoxy-2-propanol. In one aspect, the formate ester of the carrier alcohol is selected from the group consisting of formate ester of 1-propoxy-2-propanol, formate ester of diethylene glycol monomethyl ether, formate ester of bicyclo[2,2,2]-1,4-octanediol, formate ester of adamantane-1,3,5,7-tetraol, and formate ester of adamantane-1,3-diol. In one aspect, the formate ester of the carrier alcohol is selected from the group consisting formate ester of 1-propoxy-2-propanol and formate ester of diethylene glycol monomethyl ether. In one aspect, the formate ester of the carrier alcohol is selected from the group consisting of formate ester of bicyclo[2,2,2]-1,4-octanediol, formate ester of adamantane-1,3,5,7-tetraol, and formate ester of adamantane-1,3-diol.

In one aspect, the formate ester mixture comprises 10 wt. % to 99 wt. % formate ester of the carrier alcohol. Other examples of the amount of formate ester of the carrier alcohol in the formate ester mixture include 10 wt. % to 90 wt. %, 10 wt. % to 75 wt. %, 10 wt. % to 50 wt. %, 25 wt. % to 99 wt. %, 25 wt. % to 75 wt. %, 50 wt. % to 99 wt. %, and 50 wt. % to 90 wt. %. In one aspect, the formate ester mixture comprises at least 10 wt. % formate ester of the carrier alcohol. Other examples of the amount of formate ester of the carrier alcohol in the formate ester mixture include greater than 15 wt. %, 20 wt. %, 25 wt. %, 45 wt. %, 50 wt. %, 75 wt. %, and 90 wt. % formate ester of the carrier alcohol.

The formate ester mixture comprises the formate ester of the carrier alcohol and the carrier alcohol. The formate ester of the carrier alcohol and the alcohol are selected to allow a particular separation sequence in the distillation zone. The distillation zone comprises a first distillation column. In the present embodiment, (1) each of the carrier alcohol, the formate ester of the carrier alcohol, and any azeotrope formed by the formate ester of the carrier alcohol and the carrier alcohol has a boiling point temperature higher than a formic acid/water azeotrope boiling point temperature (2) the formate ester of the carrier alcohol and formic acid do not form an azeotrope and (3) the carrier alcohol and the formic acid do not form an azeotrope: conditions (1)-(3) are satisfied at an operating pressure of the first distillation column. The formate ester of the carrier alcohol and the carrier alcohol may or may not form an azeotrope. If an azeotrope is formed (i.e., any azeotrope formed), then the azeotrope has a higher boiling point than a formic acid/water azeotrope boiling point temperature at the operating pressure of the distillation column. In one aspect, the formate ester of the carrier alcohol and the carrier alcohol do not form a minimum-boiling azeotrope. In one aspect, the carrier alcohol has a higher boiling point than a boiling point temperature of the formate ester of the carrier alcohol.

The process of the present embodiment comprises feeding the formate ester mixture and water to a hydrolysis zone. The manner in which the formate ester mixture and water are fed to the hydrolysis zone is not particularly limited. In one example, the formate ester and the water are fed separately to the hydrolysis zone. In another example, the formate ester mixture and water are combined into a single feed stream and fed to the hydrolysis zone.

Within the hydrolysis zone, the formate ester of the carrier alcohol is hydrolyzed to produce the carrier alcohol and formic acid. The formate ester mixture and water are fed to the hydrolysis reaction zone wherein the formate ester of the carrier alcohol is hydrolyzed, producing a hydrolysis effluent. The hydrolysis effluent comprises the formate ester of the carrier alcohol, formic acid, water, and the carrier alcohol.

Increasing the amount of water pushes the equilibrium reaction in favor of higher conversion to formic acid. Too large an amount of water, however, can negatively impact the downstream distillation by making it impossible to recover a distillate from the first distillation column comprising a higher weight percent of formic acid than a weight percent of formic acid in a formic acid/water azeotrope at the operating pressure of the first distillation column. In one aspect, the molar ratio of water to formate ester of the carrier alcohol in the formate ester mixture fed to the hydrolysis zone ranges from 0.5:1 to 2:1. Other examples of the molar ratio of water to formate ester of the carrier alcohol ranges are from 0.5:1 to 1.5:1, or 0.5:1 to 1.4:1, or 0.5:1 to :1.3, or 1:1 to 2:1, or 1:1 to 1.5:1. One skilled in the art will understand that in some aspects, water and formate ester of an alcohol can be fed to the hydrolysis zone in recycle streams in addition to the formate ester mixture and any fresh water feed. The ratio of water to formate ester of the carrier alcohol is based upon all streams fed to the hydrolysis zone.

Unless significant hydrolysis occurs in the first distillation column, a minimum formic acid:water ratio in the hydrolysis effluent must be maintained in order to remove a first distillate comprising a higher weight percent of formic acid than a weight percent of formic acid in a formic acid/water azeotrope at an operating pressure of the first distillation column. In one aspect, the hydrolysis effluent comprises, on a carrier alcohol free basis, a higher weight percent of formic acid than the weight percent of formic acid in a formic acid/water azeotrope at the operating pressure of the first distillation column.

The operating conditions for the hydrolysis zone are not particularly limited. Hydrolysis zone temperatures can range from 40° C. to 150° C. Other examples of the hydrolysis zone temperature include 80° C. to 140° C. and 90° C. to 130° C. Hydrolysis zone operating pressure can range from 1 bara to 40 bara. Other examples of hydrolysis zone operating pressure ranges include 1 bara to 30 bara, 3 bara to 40 bara, and 3 bara to 30 bara. The hydrolysis reaction can be autocatalyzed by the formic acid. In one aspect, no component is added (e.g., homogeneous catalyst) to or included in (e.g., a heterogeneous catalyst) the hydrolysis zone. In one aspect, the rate of hydrolysis can be increased by adding an acidic catalyst. Examples of acid catalysts include formic acid (at least 1 mole % added based on moles of formate ester of the carrier alcohol in the formate ester mixture), and heterogeneous catalysts such as sulfonic acid containing resins, PFSA, and kieselguhr.

The hydrolysis zone comprises process equipment within which the hydrolysis reaction occurs. The process equipment is not particularly limited and is sized to give enough residence time to reach the desired conversion in hydrolysis. The process equipment may include one or more of a pipe, a horizontal or vertical reactor, a stirred tank reactor, a pump around loop reactor, or combinations thereof. Heat transfer area may be provided to heat or cool the contents of the hydrolysis equipment.

The process of the present invention may be conducted under continuous, semi-continuous, or batch modes of operation. The term "continuous", as used herein, refers to a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start up, reactor maintenance, or scheduled shut down periods. The term "batch" process as used herein means a process wherein all the reactants are added to the hydrolysis zone and then processed according to a predetermined course of reaction during which no material is fed into or removed from the hydrolysis zone. The term "semi-continuous" means a process where some of the reactants are charged at the beginning of the process and the remaining reactants are fed continuously as the reaction progresses.

The process comprises feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid.

The distillation zone comprises a first distillation column and the hydrolysis effluent is fed to the first distillation column. In one aspect, the distillation zone consists essentially of the first distillation column. In one aspect, the distillation zone comprises a first distillation column and a product purification column. In one aspect, the distillation zone comprises a first distillation column and a clean-up column. In one aspect, the distillation zone comprises a first distillation column, a product purification column, and a clean-up column.

The distillation zone can be designed and operated to get the desired purity of the formic acid product. In one aspect, the formic acid product comprises a higher weight percent of formic acid than a weight percent of formic acid in a formic acid/water azeotrope at the operating pressure of the first distillation column. Other examples of formic acid product composition include greater than 75 wt. % greater than 78 wt. %, greater than 80 wt. %, greater than 82 wt. %, greater than 90 wt. %, greater than 94 wt. %, greater than 95 wt. %, greater than 97 wt. %, and greater than 99 wt. % formic acid.

In one aspect, the alcohol/ester stream comprise less than 5 wt. % formic acid. Other examples of the alcohol/ester stream composition include less than 3 wt. %, 2 wt. %, 1 wt. %, 0.5 wt. %, 0.1 wt. %, 500 ppm water, and 200 ppm formic acid. In one aspect, the alcohol/ester stream comprises less than 5 wt. % water. Other examples of the alcohol/ester stream composition include less than 3 wt. %, 2 wt. %, 1 wt. %, 0.5 wt. %, 0.1 wt. %, 500 ppm, and 200 ppm water.

In one aspect, a first distillate from the first distillation column comprises a higher weight percent of formic acid than a weight percent of formic acid in a formic acid/water azeotrope at the operating pressure of the first distillation column. In one aspect, the process further comprises feeding the first distillate to a product purification column and removing the formic acid product as a product purification column distillate from the product purification column. A product purification column bottoms is also removed from the product purification column and the product purification bottoms comprises formic acid in an amount within 7 weight percentage points of an amount of formic acid in a formic acid/water azeotrope at an operating pressure of the product purification column. Other examples of the amount of formic acid in the product purification column include within 6, within 5.5, and within 5 weight percentage points of an amount of formic acid in a formic acid/water azeotrope at an operating pressure of the product purification column. The process further comprises feeding the product purification column bottoms to the first distillation column.

In one aspect, the process further comprises feeding the first bottoms to a clean-up column and removing the alcohol/ester stream as a clean-up column bottoms and removing a clean-up column distillate; and feeding the clean-up column distillate to the first distillation column.

In one aspect, the formic acid product comprises a first distillate from the first distillation column. In one aspect, the formic acid product comprises the distillate from the product purification column. In one aspect, the formic acid product comprises at least one sidedraw from the first distillation column and/or the product purification column.

The distillation column or columns can be operated continuously, semi-continuously, or batch wise as these terms are defined above. In one aspect, the distillation column(s) is operated continuously.

Each distillation column comprises a reboiler, a condenser, and at least one stage. The type of reboiler and condenser is not limited and many types are known to those skilled in the art. The number of stages for the first distillation column is not particularly limited as long as the formic acid product comprising a higher weight percent of formic acid than a weight percent of formic acid in a formic acid/water azeotrope at the operating pressure of the first distillation column and an alcohol/ester stream comprising less than 5 wt. % formic acid are produced. In one aspect, the number of theoretical stages of the first distillation column ranges from 5 to 40. Other examples of the number of theoretical stages are 10 to 30 and 10 to 15.

The operating conditions of the first distillation column are selected based on economic trade-offs with the constraint that formic acid tends to decompose at temperatures greater than about 150° C. with the rate increasing steadily as 150° C. is exceeded. In one aspect, the distillation column has a base temperature ranging from 40° C. to 150° C. Other examples of the base temperature range include from 45° C. to 125° C., 45° C. to 115° C., 45° C. to 110° C., and 45° C. to 100° C. In one aspect, the operating pressure of the first distillation column ranges from 0.05 bara to 4.0 bara. Other examples of the operating pressure range include 0.05 bara to 3.0 bara, 0.05 bara to 2.0 bara, 0.05 bara to 1.1 bara, 0.05 to 0.8 bara, 0.1 bara to 4.0 bara, 0.1 bara to 2.0 bara, 0.1 bara to 1.1 bara, 0.1 to 0.8 bara, 0.5 bara to 4.0 bara, and 0.5 bara to 2.0 bara.

In one aspect, the overall conversion of the formate ester of the carrier alcohol in the formate ester mixture to formic acid in the formic acid product ranges from 10% to 90%. Other examples of the overall conversion ranges are 10% to 75%, 20% to 80%, 20% to 60%, and 25% to 75%.

In one aspect, the hydrolysis conversion, the conversion of the formate ester of the carrier alcohol in the formate ester mixture to formic acid in the hydrolysis effluent, ranges from 10% to 75%. Other examples of the hydrolysis conversion ranges are from 10% to 60%, 10% to 50%, 10% to 40%, 20% to 60%, 20 to 50% and 20 to 40%. One skilled in the art will recognize that when the formic acid product consists of the product column distillate (i.e., no formic acid products with lower concentrations are removed from the process) the overall conversion is calculated directly using the amount of formic acid in the product column distillate. When multiple formic acid products with different formic acid concentrations are removed from the process, the overall conversion will take into account the sum of the amounts of formic acid removed in each formic acid product stream.

In one aspect, the hydrolysis reaction also occurs in the distillation zone. In other words, reaction and separation occur simultaneously in at least part of the distillation zone. In one aspect, the formate ester of the carrier alcohol further hydrolyzes in the distillation zone. In one aspect, the overall conversion of formate ester of the carrier alcohol in the formate ester mixture to formic acid in the formic acid product is up to 40 percentage points higher than the conversion of the formate ester of the carrier alcohol in the formate ester mixture to formic acid in the hydrolysis effluent. For example, if the overall conversion is 85% and the overall conversion is 40 percentage points higher than the hydrolysis conversion (i.e., the conversion of the formate ester of the carrier alcohol in the formate ester mixture to formic acid in the hydrolysis effluent), then the hydrolysis conversion is 45% (85%—40 percentage points) and the distillation conversion is 40%. In other examples, the overall conversion of formate ester of the carrier alcohol is up to 35 percentage points, 25 percentage point, 10 percentage points, of 5 percentage points higher than the hydrolysis conversion. In one aspect, the overall conversion is substantially the same as the hydrolysis conversion. The overall conversation and hydrolysis conversion are substantially the same when they are within 1.0 percent points of each other.

In another embodiment, a process for producing formic acid comprises a) feeding carbon monoxide, a fresh feed, and a catalyst feed to a carbonylation zone. The fresh feed comprises a carrier alcohol. The process comprises carbonylating the carrier alcohol to produce a formate ester of the carrier alcohol and removing a carbonylation effluent. The carbonylation effluent comprises the formate ester of the carrier alcohol, the carrier alcohol and a homogeneous catalyst. The process comprises b) feeding the carbonylation effluent to a catalyst separation zone and removing a catalyst mixture and a formate ester mixture. The catalyst mixture comprises a homogeneous catalyst and the carrier alcohol, and the formate ester mixture comprises the formate ester of the carrier alcohol. The process comprises c) feeding the formate ester mixture and water to a hydrolysis zone, hydrolyzing the formate ester of the carrier alcohol, and removing a hydrolysis effluent. The hydrolysis effluent comprises the formate ester of the carrier alcohol, formic acid, and the carrier alcohol. The process also comprises d) feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

The various aspects of the amount of formate ester of the carrier alcohol in the formate ester mixture, feeding the formate ester mixture and water to the hydrolysis zone, the molar ratio of water:formate ester of the carrier alcohol, the operating temperature and pressure of the hydrolysis zone, the composition of the formic acid product, the composition of the alcohol/ester stream, the distillation zone, the first distillation column, the product purification column, the clean-up column, the first distillation column base temperature, operating pressure, and number of theoretical stages and the overall conversion, hydrolysis conversion, and distillation conversion of formate ester of the carrier alcohol to formic acid described for the previous embodiment apply to this embodiment as well.

The process of the present embodiment comprises feeding carbon monoxide, a fresh feed, and a catalyst feed to a carbonylation zone. The fresh feed comprises a carrier alcohol. The process comprises carbonylating the carrier alcohol to produce a formate ester of the carrier alcohol and removing a carbonylation effluent. The carbonylation effluent comprises the formate ester of the carrier alcohol, the carrier alcohol, and a homogeneous catalyst.

The carbonylation process for carbonylating methanol to produce methyl formate is well known and is described in Ullmann's Encyclopedia of Industrial Chemistry (Reutemann, W.; Kieczka, H., "Formic Acid", Volume 16, 2012, Wiley-VCH Verlag GmbH & Co. KGaA, Weinheim, pp. 13-33), the entirety of which is incorporated herein by reference. In one aspect, the carbonylation zone is operated under conditions similar to those for carbonylating methanol when carbonylating the carrier alcohols of the present invention.

The carbonylation reaction is equilibrium-limited, both by carbon monoxide partial pressure and reaction temperature. Low temperature gives higher equilibrium conversion, but requires long residence times. Higher equilibrium conversion is favored by high carbon monoxide partial pressure, but requires more energy for compression of carbon monoxide and expensive vessel construction. For example, above 90% conversion of 1-propoxy-2-propanol is achievable at close to room temperature and around 150 bara CO pressure, but a reaction time around 12 hours is needed to reach equilibrium conversion, depending upon catalyst convesion. Thus, tradeoffs are required for economical production of formate ester via carbonylation of the carrier alcohol. The carbonylation is typically carried out at a total pressure (comprising carbon monoxide, carrier alcohol, and formate ester partial pressures at reaction temperature) of 15 to 150 bara, more typically 20 to 80 bara. Temperature of the carbonylation zone may be 20° C. to 140° C., more typically 40° C. to 110° C. The carbonylation is typically carried out with the use of a homogeneous basic catalyst, although use of heterogeneous basic catalysts is known in the art (see for example, Di Girolamo, M.; Marchionna, M., "Acidic and Basic Ion Exchange Resins for Industrial Applications", Journal of Molecular Catalysis A: Chemical 177 (2001) 33-40). In one aspect, the homogeneous catalyst comprises the potassium, sodium, or cesium salt of the carrier alcohol, i.e., alkali alkoxides. Catalyst concentration may vary widely, ranging from 0.1 to 7.5 wt. %, based on liquids fed to the carbonylation zone, as molecular mass of the alkali salt of the carrier alcohol may vary widely. Potassium alkoxides are preferred, as they offer acceptable tradeoffs between cost, catalytic activity, and solubility in the carrier alcohol. Typical concentrations for potassium salts are 0.1 to 5 wt. %, more typically 0.2 to 1.5 wt. %, based on liquids fed to the carbonylation zone. The carbonylation reaction is exothermic and equilibrium conversion is retarded by high temperature. Thus, management of the heat of reaction is important. The heat management may be accomplished by any method known in the art. The reaction may be conducted adiabatically, partially adiabatically, or isothermally, batch or continuously. When run adiabatically or partially adiabatically, the liquids fed to the carbonylation zone must be sufficiently cool to allow for heat rise due to reaction. Typically, the liquid feeds must be cooled at least 10° C., more typically at least 20° C., below the desired adiabatic outlet temperature. Alternatively, heat may be removed while the reaction is carried out, typically within a heat exchanger of any type known in the art, such as shell and tube exchangers, spiral wound exchangers, plate exchangers, and the like. If the desired reaction temperature is sufficiently high, for example above about 90° C., the heat may be removed by generation of steam or other vapors in a boiler-type heat exchanger. The generated steam or vapors may be used as a heat source in other sections of the formic acid production process where energy is required. For example, the steam or vapors may be used to drive the distillation column used to recover formic acid generated in the hydrolysis of the formate ester of the carrier alcohol.

The process comprises feeding the carbonylation effluent to a catalyst separation zone and removing a catalyst mixture and a formate ester mixture. The catalyst mixture comprises the homogeneous catalyst and the carrier alcohol and the formate ester mixture comprises the formate ester of the carrier alcohol. The manner in which the homogeneous catalyst is separated from the carbonylation effluent is not very limited. Examples of suitable processes for separating the homogeneous catalyst from the carbonylation effluent include, single stage flash distillation, fractional distillation, membrane permeation, extraction, and neutralization of the alkali alkoxide catalyst with an acid. The catalyst separation zone may comprise one or more of these separation process. In one aspect, essentially all of the homogeneous catalyst leaves the catalyst separation zone in the catalyst mixture.

In one aspect, the catalyst separation zone comprises a flash vessel maintained at an operating pressure below the operating pressure of the carbonylation zone. The carbonylation effluent is fed to the flash vessel and a vapor stream leaving the flash vessel is condensed and removed from the catalyst recovery zone as the formate ester mixture. The catalyst mixture, comprising the homogeneous catalyst and the carrier alcohol, leaves the bottom of the flash vessel. Often the boiling points of the carrier alcohol and the formate ester of the carrier alcohol are too close together to allow effective separation of the majority of the carrier alcohol from the formate ester. In one aspect, the carbonylation effluent is fed to a fractional distillation column to enrich the amount of formate ester of the carrier alcohol in the formate ester mixture. The distillation is typically carried out in a column comprising 5 to 75 theoretical stages, more typically 10 to 50 theoretical stages, with a reflux ratio of 0.5 to 5, more typically a reflux ratio of 1 to 3. In both flash distillation and fractional distillation, active catalyst, i.e., alkali alkoxide may be present in mixtures being distilled. The carbonylation reaction is reversible, and with the low partial pressure of carbon monoxide prevalent at distillation condition, the formate ester may partially decompose back to the carrier alcohol and carbon monoxide. In order to minimize such decomposition, the distillation is preferably carried out with low residence time in the sections of the column (i.e., below the feed) and reboiler where catalyst is present, and at low temperatures. Residence times of less than 30 minutes, more preferably less than 10 minutes, are desirable. Favorable reboiler temperatures are 10 to 50° C. less than those temperatures employed in the carbonylation zone. Often such low reboiler temperatures require use of vacuum operation for the distillation. Desired vacuum distillation pressures range from 0.025 bara to 0.99 bara, more typically 0.04 to 0.66 bara.

In one aspect, the catalyst feed comprises the catalyst mixture.

In one aspect, the formate ester mixture comprises 10 wt. % to 99 wt. % formate ester of the carrier alcohol. Other examples of the amount of formate ester of the carrier alcohol in the formate ester mixture include 10 wt. % to 90 wt. %, 10 wt. % to 75 wt. %, 10 wt. % to 50 wt. %, 25 wt. % to 99 wt. %, 25 wt. % to 75 wt. %, and 50 wt. % to 99 wt. %. In one aspect, the formate ester mixture comprises at least 20 wt. % formate ester of the carrier alcohol. Other examples of the amount of formate ester of the carrier alcohol in the formate ester mixture include at least 25 wt. %, 45 wt. %, 50 wt. %, 75 wt. %, and 90 wt. % formate ester of the carrier alcohol.

In one aspect, the carrier alcohol has a boiling point temperature higher than a boiling point temperature of the formate ester of the carrier alcohol at an operating pressure of the catalyst separation zone. In one aspect, greater than 50% of the carrier alcohol that enters the catalyst separation zone leaves in the catalyst mixture. Other examples of the fraction of carrier alcohol that leaves the catalyst separation zone in the catalyst mixture are greater than 60%, greater than 70%, and greater than 80%.

In one aspect, the carrier alcohol is a compound comprising at least one OH group and 5 to 14 carbon atoms. Other examples of the carrier alcohol size include 5 to 12 and 5 to 10 carbon atoms. The carrier alcohol has a higher boiling point temperature than a boiling point temperature of the formic acid/water azeotrope at the operating pressure of the first distillation column which separates formic acid from the carrier alcohol and formate ester of the carrier alcohol in the hydrolysis effluent. Furthermore, the carrier alcohol and the formate ester of the carrier alcohol do not form azeotropes with formic acid.

Non-limiting examples of favorable high-boiling carrier alcohols for the present invention are ethylene glycol, 1,2-propanediol, 1,3-propanediol, 1,2-butanediol, 1,3-butanediol, 2,3-butanediol, 1,4-butanediol, 1,2-cyclohexanediol, 1,3-cyclohexanediol, 1,4-cyclohexanediol, 1,2-phenylenedimethanol, 1,3-phenylenedimethanol, 1,4-phenylenedimethanol, 1,2-cyclohexanedimethanol, 1,3-cyclohexanedimethanol, 1,4-cyclohexanedimethanol, 2,2,4-trimethylpentane-1,3-diol, bicyclo[2,2,2]-1,4-octanediol, adamantane-1,3,5,7-tetraol, adamantane-1,3-diol; $C_3$ to $C_8$ triols and polyols, such as glycerol, trimethylolethane, trimethylolpropane, trimethylolbutane; glycol ethers, such as diethylene glycol, triethylene glycol, and di and tri oligomers of propanediols and butanediols; and $C_1$ to $C_6$ alkoxy ethers of diols, glycol ethers, triols and polyols, such as diethylene glycol monomethyl ether, diethylene glycol monoethyl ether, diethylene glycol monopropyl ether, diethylene glycol monobutyl ether, 1-ethoxy-2-propanol, 1-propoxy-2-propanol, 1-butoxy-2-propanol, 2-ethoxy-1-propanol, 2-propoxy-1-propanol, 2-butoxy-1-propanol. Furthermore, if the carrier alcohol contains more than one hydroxyl group, the carrier alcohol may be partially esterified. Thus, monoformate esters of diols, triols, and polyols, such as ethylene glycol monoformate, diethylene glycol monoformate, 2-hydroxy-propylformate, are useful for the present invention.

In one aspect, high-boiling carrier alcohols contain secondary alcohol groups, such as 1-ethoxy-2-propanol, 1-propoxy-2-propanol, 1-butoxy-2-propanol, and monoformate esters of diols with unexpectedly high hydrolysis equilibrium molar ratios for hydrolysis of the diformate ester, such as ethylene glycol monoformate, diethylene glycol monoformate, 2-hydroxy-propylf formate. In one aspect, the carrier alcohol is selected from the group consisting of [2,2,2]-bicyclo-1,4-octanediol, adamantine-1,3,5, 7-tetraol, and adamantane-1,3-diol.

In one aspect, the carrier alcohol is selected from the group consisting of ethylene glycol; 1,2-propanediol; 1,3-propanediol; 1,2-butanediol; 1,3-butanediol; 2,3-butanediol; 1,4-butanediol; 1,2-cyclohexanediol; 1,3-cyclohexanediol; 1,4-cyclohexanediol; 1,2-phenylenedimethanol; 1,3-phenylenedimethanol; 1,4-phenylenedimethanol; 1,2-cyclohexanedimethanol; 1,3-cyclohexanedimethanol; 1,4-cyclohexanedimethanol; 2,2,4-trimethylpentane-1,3-diol; glycerol; trimethylolethane; trimethylolpropane; trimethylolbutane; diethylene glycol; triethylene glycol; di and tri oligomers of propanediols and butanediols; diethylene glycol monomethyl ether; diethylene glycol monoethyl ether; diethylene glycol monopropyl ether; diethylene glycol monobutyl ether; 1-ethoxy-2-propanol; 1-propoxy-2-propanol; 1-butoxy-2-propanol; 2-ethoxy-1-propanol; 2-propoxy-1-propanol; 2-butoxy-1-propanol; ethylene glycol monoformate; diethylene glycol monoformate; and 2-hydroxypropylformate. In one aspect, the carrier alcohol is selected from the group consisting of ethylene glycol; 1,2-propanediol; 1,3-propanediol; 1,2-butanediol; 1,3-butanediol; 2,3-butanediol; 1,4-butanediol; 1,2-cyclohexanediol; 1,3-cyclohexanediol; 1,4-cyclohexanediol; 1,2-phenylenedimethanol; 1,3-phenylenedimethanol; 1,4-phenylenedimethanol; 1,2-cyclohexanedimethanol; 1,3-cyclohexanedimethanol; 1,4-cyclohexanedimethanol; and 2,2,4-trimethylpentane-1,3-diol. In one aspect, the carrier alcohol is selected from the group consisting of glycerol; trimethylolethane; trimethylolpropane; trimethylolbutane; diethylene glycol; triethylene glycol; and di and tri oligomers of propanediols and butanediols. In one aspect, the carrier alcohol is selected from the group consisting of diethylene glycol monomethyl ether; diethylene glycol monoethyl ether; diethylene glycol monopropyl ether; diethylene glycol monobutyl ether; 1-ethoxy-2-propanol; 1-propoxy-2-propanol; 1-butoxy-2-propanol; 2-ethoxy-1-propanol; 2-propoxy-1-propanol; and 2-butoxy-1-propanol.

In one aspect, the carrier alcohol is selected from the group consisting of ethylene glycol; diethylene glycol; diethylene glycol monomethyl ether; 1,2-propane diol; 1-propoxy-2-propanol; 2-hydroxy-propanol; 1-ethoxy-2propanol, and 1-butoxy-2-propanol. In one aspect, the carrier alcohol is selected from the group consisting of ethylene glycol, diethylene glycol monomethyl ether, diethylene glycol, and 1-propoxy-2-propanol.

In one aspect, the formic acid product comprises greater than 95 wt. %, formic acid and the alcohol/ester stream comprises less than 0.5 wt. % formic acid and less than 200 ppm water, and the process further comprises feeding the alcohol/ester stream to the carbonylation zone in step a).

In one aspect, the formate ester mixture comprises at least 50 wt. % formate ester of the carrier alcohol.

In one aspect, a molar ratio of water:formate ester of the carrier alcohol fed to the hydrolysis zone ranges from 1:1 to 3:1.

In one aspect, the formic acid product comprises a distillate from the first distillation column. In one aspect, a first distillate from the first distillation column comprises a higher weight percent of formic acid than a weight percent of formic acid in a formic acid/water azeotrope at the operating pressure of the first distillation column. The process further comprises feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column and feeding the product purification bottoms to the first distillation column.

In one aspect, the first distillation column has a base temperature from 60° C. to 150° C., the operating pressure of the distillation column ranges from 0.4 bara to 4 bara, and the distillation column comprises from 10 to 40 theoretical stages.

In one aspect, the process further comprises feeding the alcohol/ester stream to the carbonylation zone in step a).

In one aspect, an overall conversion of the formate ester of the carrier alcohol in the formate ester mixture to formic acid in the formic acid product ranges from 40% to 90%.

In yet another embodiment, a process for producing formic acid comprises a) feeding methanol, an alcohol feed, and a catalyst recycle to a dehydrogenative coupling (DHC) zone. The alcohol feed comprises a carrier alcohol and less than 1 wt. % water. The process comprises performing a DHC reaction of methanol with the carrier alcohol to produce a formate ester of the carrier alcohol, and removing a DHC effluent. The DHC effluent comprises the formate ester of the carrier alcohol and a homogeneous catalyst. The process comprises b) feeding the DHC effluent to a catalyst separation zone and removing the catalyst recycle and a formate ester mixture. The catalyst recycle comprises the homogeneous catalyst, and the formate ester mixture comprises the formate ester of the carrier alcohol. The process comprises c) feeding the formate ester mixture and water to a hydrolysis zone, hydrolyzing the formate ester of the carrier alcohol, and removing a hydrolysis effluent. The hydrolysis effluent comprises the formate ester of the carrier alcohol, formic acid, and the carrier alcohol. The process also comprises d) feeding the hydrolysis effluent to a distillation zone and removing a formic acid product and an alcohol/ester stream. The formic acid product comprises greater than 75 wt. % formic acid and the alcohol/ester stream comprises less than 5 wt. % formic acid. The carrier alcohol is selected from the group consisting of $C_5$ to $C_{14}$ secondary and tertiary alcohols. The distillation zone comprises a first distillation column and the hydrolysis effluent is fed to the first distillation column. At the operating pressure of the first distillation column, (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope.

The various aspects of the amount of formate ester of the carrier alcohol in the formate ester mixture, feeding the formate ester mixture and water to the hydrolysis zone, the molar ratio of water:formate ester of the carrier alcohol, the operating temperature and pressure of the hydrolysis zone, the composition of the formic acid product, the composition of the alcohol/ester stream, the distillation zone, the first distillation column, the product purification column, the clean-up column, the first distillation column base temperature, operating pressure, and number of theoretical stages, and the overall conversion, hydrolysis conversion, and distillation conversion of formate ester of the carrier alcohol to formic acid described for the previous embodiment apply to this embodiment as well.

In the present embodiment, a process for producing formic acid comprises feeding methanol, an alcohol feed, and a catalyst recycle to a dehydrogenative coupling (DHC) zone. The alcohol feed comprises the carrier alcohol and less than 1 wt. % water. The process comprises performing a DHC reaction of methanol with the carrier alcohol to produce a formate ester of the carrier alcohol and hydrogen, and removing a DHC effluent. The process of preparing a formate ester of the carrier alcohol by contacting methanol with the carrier alcohol in the presence of an iron-based catalyst is described in detail in U.S. Application No. 62/540,317, filed on the same day as the present application, the content of which is hereby incorporated by reference in its entirety.

In one aspect, the catalyst or catalyst precursor(s) is/are combined with methanol and the carrier alcohol selected from the group consisting of $C_5$ to $C_{14}$ secondary and tertiary alcohols, and optionally a solvent and/or a hydrogen acceptor, at a catalyst-to-methanol weight ratio of 1:10 to 1:100,000 in a reactor. The mixture is heated with mixing to a temperature of 40 to 160° C. for a period of 1-6 hours during which time hydrogen ($H_2$) may evolve, and may be removed from the reactor. It is possible to carry the reaction to full conversion, but it may be advantageous to limit the conversion due to rates and reaction pressures.

The process comprises removing the homogeneous catalyst from the DHC effluent prior to hydrolyzing the formate ester of the carrier alcohol. The manner in which the homogeneous catalyst is removed is not very limited. In one aspect, the catalyst separation zone comprises a flash vessel maintained at an operating pressure below the operating pressure of the DHC zone. The DHC effluent is fed to the flash vessel and a vapor stream leaving the flash vessel is condensed and removed from the catalyst separation zone as the formate ester mixture. The catalyst recycle, comprising the homogeneous catalyst, leaves the bottom of the flash vessel. In one aspect, essentially all of the homogeneous catalyst leaves the catalyst separation zone in the catalyst recycle. In one aspect, the DHC effluent is fed to a distillation column to enrich the amount of formate ester of the alcohol in the formate ester mixture. The distillation column is operated with temperatures below about 170° C. or about 110° C. where catalyst and formate ester of the alcohol are stable. The distillation column is operated at pressures less than 3 bara or ranging from 1.5 to 0.04 bara. In another aspect, the homogeneous catalyst is concentrated in the retentate of a membrane permeation process, and the permeate comprises the formate ester mixture.

In one aspect, the carrier alcohol is selected from the group consisting of 1-popoxy-2-propanol, 1-ethoxy-2-propanol, [2,2,2]-bicyclo-1,4-octanediol, adamantane-1,3,5,7-tetraol, and adamantine-1,3-diol. In one aspect, the carrier alcohol is selected from the group consisting of 1-popoxy-2-propanol and 1-ethoxy-2-propanol. In one aspect, the carrier alcohol is selected from the group consisting of [2,2,2]-bicyclo-1,4-octanediol, adamantane-1,3,5,7-tetraol, and adamantine-1,3-diol. In one aspect, the carrier alcohol is 1-popoxy-2-propanol. In one aspect, the carrier alcohol is 1-ethoxy-2-propanol. In one aspect, the carrier alcohol is [2,2,2]-bicyclo-1,4-octanediol. In one aspect, the carrier alcohol is adamantane-1,3,5,7-tetraol. In one aspect, the carrier alcohol is adamantine-1,3-diol.

In one aspect, the formic acid product comprises greater than 95 wt. %, formic acid and the alcohol/ester stream comprises less than 0.5 wt. % formic acid and less than 200 ppm water, and the alcohol feed comprises the alcohol/ester stream.

In one aspect, a molar ratio of water:formate ester of the carrier alcohol fed to the hydrolysis zone ranges from 1:1 to 3:1.

In one aspect, a first distillate from the first distillation column comprises a higher weight percent of formic acid than a weight percent of formic acid in a formic acid/water azeotrope at the operating pressure of the first distillation column. The process further comprises feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column, and feeding the product purification column bottoms to the first distillation column.

Listed below are non-limiting embodiments A1-A25.

A1. A process for recovering formic acid from a formate ester mixture, the process comprising
  a) feeding the formate ester mixture and water to a hydrolysis zone, wherein the formate ester mixture comprises a formate ester of a carrier alcohol and the carrier alcohol;
  b) hydrolyzing the formate ester mixture in the hydrolysis zone to produce a hydrolysis effluent comprising the formate ester of the carrier alcohol, formic acid, and the carrier alcohol; and
  c) feeding the hydrolysis effluent to a distillation zone, and removing a formic acid product and an alcohol/ester stream, wherein the formic acid product comprises a higher weight percent of formic acid than a weight percent of formic acid in a formic acid/water azeotrope at the operating pressure of the first distillation column and the alcohol/ester stream comprises the carrier alcohol, the formate ester of the carrier alcohol, and less than 5 wt. % formic acid,
wherein the distillation zone comprises a first distillation column and the hydrolysis effluent is fed to the first distillation column, and
wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope, with (1)-(3) being satisfied at an operating pressure of the first distillation column.

A2. The process of embodiment A1, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

A3. The process of any of embodiments A1-A2, wherein the alcohol/ester stream comprises less than 3 wt. %, 2 wt. %, 1 wt. %, 0.5 wt. %, 0.1 wt. %, 500 ppm, or 200 ppm formic acid.

A4. The process of any of embodiments A1-A3, wherein the alcohol ester stream comprises less than 5 wt. %, 3 wt. %, 2 wt. %, 1 wt. %, 0.5 wt. %, 0.1 wt. %, 500 ppm water, or 200 ppm water.

A5. The process of any of embodiments A1-A4, wherein the formate ester mixture comprises at least 20 wt. %, 25 wt. %, 45 wt. %, 50 wt. %, 75 wt. %, or 90 wt. % formate ester of the carrier alcohol.

A6. The process of any of embodiments A1-A5, wherein a molar ratio of water:formate ester of the carrier alcohol fed to the hydrolysis zone ranges from 0.5:1 to 2:1, or 0.8:1 to 1.5:1, or 1.1:1 to 1.4:1.

A7. The process of any of embodiments A1-A6, wherein carrier alcohol is selected from the group consisting of [2,2,2]-bicyclo-1,4-octanediol, adamantane-1,3,5,7-tetraol, and adamantine-1,3-diol.

A8. The process of any of embodiments A1-A6, wherein the formate ester is selected from the group consisting of formate ester of ethylene glycol, formate ester of 1,2-propanediol, formate ester of 1,3-propanediol, formate ester of 1,2-butanediol, formate ester of 1,3-butanediol, formate ester of 2,3-butanediol, formate ester of 1,4-butanediol, formate ester of 1,2-cyclohexanediol, formate ester of 1,3-cyclohexanediol, formate ester of 1,4-cyclohexanediol, formate ester of 1,2-phenylenedimethanol, formate ester of 1,3-phenylenedimethanol, formate ester of 1,4-phenylenedimethanol, formate ester of 1,2-cyclohexanedimethanol, formate ester of 1,3-cyclohexanedimethanol, formate ester of 1,4-cyclohexanedimethanol, and formate ester of 2,2,4-trimethylpentane-1,3-diol.

A9. The process of any of embodiments A1-A6, wherein the formate ester is 1-propoxy-2-propyl formate.

A10. The process of any of embodiments A1-A6, wherein the formate ester is selected from the group consisting of formate ester of diethylene glycol monomethyl ether; formate ester of diethylene glycol monoethyl ether; formate ester of diethylene glycol monopropyl ether; formate ester of diethylene glycol monobutyl ether; formate ester of 1-ethoxy-2-propanol; formate ester of 1-propoxy-2-propanol; formate ester of 1-butoxy-2-propanol; formate ester of 2-ethoxy-1-propanol; formate ester of 2-propoxy-1-propanol; formate ester of 2-butoxy-1-propanol.

A11. The process of any of embodiments A1-A6, wherein the formate ester is selected from the group consisting of formate ester of ethylene glycol; formate ester of diethylene glycol; formate ester of diethylene glycol monomethyl ether; formate ester of 1,2-propane diol; formate ester of 1-propoxy-2-propanol; formate ester of 2-hydroxy-propanol; formate ester of 1-ethoxy-2propanol, and formate ester of 1-butoxy-2-propanol.

A12. The process of any of embodiments A1-6, wherein the formate ester is selected from the group consisting of formate ester of ethylene glycol; formate ester of diethylene glycol; formate ester of diethylene glycol monomethyl ether; and formate ester of 1-propoxy-2-propanol.

A13. The process of any of embodiments A1-A6, wherein the formate ester is selected from the group consisting of the formate ester of 1-propoxy-2-propanol, formate ester of diethylene glycol monomethyl ether, formate ester of ethylene glycol, and formate ester of diethylene glycol.

A14. The process of any of embodiments A1-A13, wherein the hydrolysis zone operates at a temperature from 40° C. to 140° C. and at a pressure from 1 bara to 20 bara.

A15. The process of any of embodiments A1-A14, wherein the hydrolysis zone comprises a hydrolysis catalyst.

A16. The process of any of embodiments A1-A15, wherein the formic acid product comprises a distillate from the first distillation column and/or the alcohol/ester stream comprises a bottoms from the first distillation column.

A17. The process of any of embodiments A1-A16, wherein a first distillate from the first distillation column comprises a higher weight percent of formic acid than a weight percent of formic acid in a formic acid/water azeotrope at the operating pressure of the first distillation column; the process further comprising
- d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and
- e) feeding the product purification column bottoms to the first distillation column.

A18. The process of any of embodiments A1-A17, further comprising removing a first bottoms from the first distillation column and
- f) feeding the first bottoms to a clean-up column and removing the alcohol/ester stream as a clean-up column bottoms and removing a clean-up column distillate; and
- g) feeding the clean-up column distillate to the first distillation column.

A19. The process of any of embodiments A1-A18, wherein an overall conversion of formate ester of the carrier alcohol in the formate ester mixture to formic acid in the formic acid product ranges from 10% to 90%, 10% to 75%, or 20% to 60%.

A20. The process of any of embodiments A1-A19, wherein the formate ester of the carrier alcohol in the hydrolysis effluent further hydrolyzes in the distillation zone.

A21. The process of embodiment A20, wherein an overall conversion of formate ester of the carrier alcohol to formic acid in the formic acid product ranges from 2 to 40 percentage points, 2 to 20 percentage points, or 2 to 10 percentage points higher than the hydrolysis conversion of formate ester of the carrier alcohol to formic acid.

A22. The process of any of embodiments A1-A21, wherein the first distillation column has a base temperature from 40° C. to 150° C., 45° C. to 125° C., or 45° C. to 100° C., and the operating pressure of the first distillation column ranges from 0.05 bara to 4 bara, 0.05 bara to 3 bara, or 0.1 bara to 2 bara.

A23. The process of any of embodiments A1-A22, wherein the first distillation column comprises from 5 to 40, 10 to 30 or 10 to 15 theoretical stages.

A24. The process of any of embodiments A1-A23, further comprising
- h) feeding carbon monoxide, a fresh feed, and a catalyst feed, to a carbonylation zone, wherein the fresh feed comprises a carrier alcohol, carbonylating the carrier alcohol to produce the formate ester of the carrier alcohol, and removing a carbonylation effluent comprising the formate ester of the carrier alcohol, the carrier alcohol, and a homogeneous catalyst; and
- i) feeding the carbonylation effluent to a catalyst separation zone and removing a catalyst mixture and the formate ester mixture, wherein the catalyst mixture comprises the homogeneous catalyst and the carrier alcohol.

A25. The process of any of embodiments A1-A23, further comprising
- h) feeding methanol, an alcohol feed, and a catalyst recycle to a dehydrogenative coupling (DHC) zone, performing a DHC reaction of methanol with the carrier alcohol to produce a formate ester of the carrier alcohol and hydrogen, and removing a DHC effluent comprising the formate ester of the carrier alcohol and a homogeneous catalyst; and
- i) feeding the DHC effluent to a catalyst separation zone and removing the catalyst recycle and the formate ester mixture, wherein the catalyst recycle comprises the homogeneous catalyst.

Listed below are non-limiting embodiments B1-B26.

B1. A process for producing formic acid, wherein the process comprises,
- a) feeding carbon monoxide, a fresh feed, and a catalyst feed to a carbonylation zone, wherein the fresh feed comprises a carrier alcohol, carbonylating the carrier alcohol to produce a formate ester of the carrier alcohol, and removing a carbonylation effluent comprising the formate ester of the carrier alcohol, the carrier alcohol, and a homogeneous catalyst;
- b) feeding the carbonylation effluent to a catalyst separation zone and removing a catalyst mixture and a formate ester mixture, wherein the catalyst mixture comprises the homogeneous catalyst and the carrier alcohol and wherein the formate ester mixture comprises the formate ester of the carrier alcohol;
- c) feeding the formate ester mixture and water to a hydrolysis zone, hydrolyzing the formate ester of the carrier alcohol, and removing a hydrolysis effluent comprising the formate ester of the carrier alcohol, formic acid, and the carrier alcohol; and
- d) feeding the hydrolysis effluent to a distillation zone and removing a formic acid product and an alcohol/ester stream, wherein the formic acid product comprises a higher weight percent of formic acid than a weight percent of formic acid in a formic acid/water azeotrope at an operating pressure of a first distillation column and the alcohol/ester stream comprises less than 5 wt. % formic acid;

wherein the distillation zone comprises the first distillation column and the hydrolysis effluent is fed to the first distillation column, and wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and the formic acid do not form an azeotrope, with (1)-(3) being satisfied at the operating pressure of the first distillation column.

B2. The process of embodiment B1, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

B3. The process of any of embodiments B1-B2, wherein the alcohol/ester stream comprises less than 3 wt. %, 2 wt. %, 1 wt. %, 0.5 wt. %, 0.1 wt. %, 500 ppm, or 200 ppm formic acid.

B4. The process of any of embodiments B1-B3 wherein the alcohol/ester stream comprises less than 5 wt. %, 3 wt. %, 2 wt. %, 1 wt. %, 0.5 wt. %, 0.1 wt. %, 500 ppm water, or 200 ppm water.

B5. The process of any of embodiments B1-B4, wherein the formate ester mixture comprises at least 20 wt. %, 25 wt. %, 45 wt. %, 50 wt. %, 75 wt. %, or 90 wt. % formate ester of the carrier alcohol.

B6. The process of any of embodiments B1-B5, wherein a molar ratio of water:formate ester of the carrier alcohol fed to the hydrolysis zone ranges from 0.5:1 to 2:1, or 0.8:1 to 1.5:1, or 1.1:1 to 1.4:1.

B7. The process of any of embodiments B1-B6, wherein the carrier alcohol is selected from the group consisting of 1,2-propanediol; 1,3-propanediol; 1,2-butanediol; 1,3-butanediol; 2,3-butanediol; 1,4-butanediol; 1,2-cyclohexanediol; 1,3-cyclohexanediol; 1,4-cyclohexanediol; 1,2-phenylenedimethanol; 1,3-phenylenedimethanol; 1,4-phenylenedimethanol; 1,2-cyclohexanedimethanol; 1,3-cyclohexanedimethanol; 1,4-cyclohexanedimethanol; 2,2,4-trimethylpentane-1,3-diol; glycerol; trimethylolethane; trimethylolpropane; trimethylolbutane; diethylene glycol; triethylene glycol; di and tri oligomers of propanediols and butanediols; diethylene glycol monomethyl ether; diethylene glycol monoethyl ether; diethylene glycol monopropyl ether; diethylene glycol monobutyl ether; 1-ethoxy-2-propanol; 1-propoxy-2-propanol; 1-butoxy-2-propanol; 2-ethoxy-1-propanol; 2-propoxy-1-propanol; 2-butoxy-1-propanol; ethylene glycol monoformate; diethylene glycol monoformate; and 2-hydroxy-propylformate.

B8. The process of any of embodiments B1-B7, wherein the carrier alcohol is selected from the group consisting of ethylene glycol; 1,2-propanediol; 1,3-propanediol; 1,2-butanediol; 1,3-butanediol; 2,3-butanediol; 1,4-butanediol; 1,2-cyclohexanediol; 1,3-cyclohexanediol; 1,4-cyclohexanediol; 1,2-phenylenedimethanol; 1,3-phenylenedimethanol; 1,4-phenylenedimethanol; 1,2-cyclohexanedimethanol; 1,3-cyclohexanedimethanol; 1,4-cyclohexanedimethanol; and 2,2,4-trimethylpentane-1,3-diol.

B9. The process of any of embodiments B1-B6, wherein the carrier alcohol is selected from the group consisting of glycerol; trimethylolethane; trimethylolpropane; trimethylolbutane; diethylene glycol; triethylene glycol; and di and tri oligomers of propanediols and butanediols.

B10. The process of any of embodiments B1-B6, wherein the carrier alcohol is selected from the group consisting of diethylene glycol monomethyl ether; diethylene glycol monoethyl ether; diethylene glycol monopropyl ether; diethylene glycol monobutyl ether; 1-ethoxy-2-propanol; 1-propoxy-2-propanol; 1-butoxy-2-propanol; 2-ethoxy-1-propanol; 2-propoxy-1-propanol; and 2-butoxy-1-propanol.

B11. The process of any of embodiments B1-B6, wherein the carrier alcohol is selected from the group consisting of ethylene glycol; diethylene glycol; diethylene glycol monomethyl ether; 1,2-propane diol; 1-popoxy-2-propanol; 2-hydroxy-propanol; 1-ethoxy-2propanol, and 1-butoxy-2-propanol.

B12. The process of embodiment B11, wherein the carrier alcohol is selected from the group consisting of ethylene glycol, diethylene glycol monomethyl ether, diethylene glycol, and 1-propoxy-2-propanol.

B13. The process of any of embodiments B1-B6, wherein carrier alcohol is selected from the group consisting of [2,2,2]-bicyclo-1,4-octanediol, adamantane-1,3,5,7-tetraol, and adamantane-1,3-diol; or the carrier alcohol is [2,2,2]-bicylco-1,4-octanediol; or the carrier alcohol is adamantane-1,3,5,7-tetraol; or the carrier alcohol is adamantane-1,3-diol.

B14. The process of any of embodiments B1-B13, wherein the carrier alcohol has a boiling point temperature higher than a boiling point temperature of the formate ester of the carrier alcohol at an operating pressure of the catalyst separation zone.

B15. The process of any of embodiments B1-B14, wherein the hydrolysis zone operates at a temperature from 40° C. to 140° C. and at a pressure from 1 bara to 40 bara.

B16. The process of any of embodiments B1-B15, wherein the hydrolysis zone comprises a hydrolysis catalyst.

B17. The process of any of embodiments B1-B16, wherein an overall conversion of formate ester of the carrier alcohol in the formate ester mixture to formic acid in the formic acid product ranges from 10% to 90%, 10% to 75%, or 20% to 60%.

B18. The process of any of embodiments B1-B17, wherein the formate ester of the carrier alcohol in the hydrolysis effluent further hydrolyzes in the distillation column.

B19. The process of embodiment B18, wherein an overall conversion of formate ester of the carrier alcohol to formic acid ranges from 2 to 40 percentage points, 2 to 20 percentage points, or 2 to 10 percentage points higher than the hydrolysis conversion of formate ester of the carrier alcohol to formic acid.

B20. The process of any of embodiments B1-B18, wherein the first distillation column has a base temperature from 40° C. to 150° C., 45° C. to 125° C., or 45° C. to 100° C., and the operating pressure of the first distillation column ranges from 0.05 bara to 4 bara, 0.05 bara to 3 bara, or 0.1 bara to 2 bara.

B21. The process of any of embodiments B1-B20, wherein the first distillation column comprises from 5 to 40, 10 to 30, or 10 to 15 theoretical stages.

B22. The process of any of embodiments B1-B21, wherein a first distillate from the first distillation column comprises a higher weight percent of formic acid than a weight percent of formic acid in a formic acid/water azeotrope at the operating pressure of the first distillation column; the process further comprising
  d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and
  e) feeding the product purification column bottoms to the first distillation column.

B23. The process of any of embodiments B1-B22, further comprising removing a first bottoms from the first distillation column, and f) feeding the first bottoms to a clean-up column and removing the alcohol/ester stream as a clean-up column bottoms and removing a clean-up column distillate; and
  g) feeding the clean-up distillate to the first distillation column.

B24. The process of any of embodiments B1-B23, wherein the catalyst feed comprises the catalyst mixture.

B25. The process of any of embodiments B1-B24, wherein the carrier alcohol feed comprises the alcohol/ester stream.

B26. The process of any of embodiments B1-B25, wherein the formic acid product comprises a first distillate of the first distillation column Listed below are non-limiting embodiments C1-C23.

C1. A process for producing formic acid, wherein the process comprises,
  a) feeding methanol, an alcohol feed, and a catalyst recycle, to a dehydrogenative coupling (DHC) zone, wherein the carrier alcohol feed comprises the carrier alcohol and less than 1 wt. % water, performing a DHC reaction of the methanol and the carrier alcohol to produce a formate ester of the carrier alcohol and hydrogen, and removing a DHC effluent comprising the formate ester of the carrier alcohol, the carrier alcohol, and a homogeneous catalyst;

b) feeding the DCH effluent to a catalyst separation zone and removing the catalyst recycle and a formate ester mixture, wherein the catalyst recycle comprises the homogeneous catalyst and the carrier alcohol, and wherein the formate ester mixture comprises the formate ester of the carrier alcohol;

c) feeding the formate ester mixture and water to a hydrolysis zone, hydrolyzing the formate ester of the carrier alcohol, and removing a hydrolysis effluent comprising the formate ester of the carrier alcohol, formic acid, and the carrier alcohol; and d) feeding the hydrolysis effluent to a distillation zone, and removing a formic acid product and an alcohol/ester stream, wherein the formic acid product comprises a higher weight percent formic acid that a weight percent of formic acid at an operating pressure of a first distillation column, and the alcohol/ester stream comprises the carrier alcohol, the formate ester of the carrier alcohol, and less than 5 wt. % formic acid, wherein the carrier alcohol is selected from the group consisting of 05 to 014 secondary and tertiary alcohols, wherein the distillation zone comprises the first distillation column and the hydrolysis effluent is fed to the first distillation column, wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope, with (1)-(3) being satisfied at the operating pressure of the first distillation column.

C2. The process of embodiment C1, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

C3. The process of any of embodiments C1-C2, wherein the alcohol/ester stream comprises less than 3 wt. %, 2 wt. %, 1 wt. %, 0.5 wt. %, 0.1 wt. %, 500 ppm, or 200 ppm formic acid.

C4. The process of any of embodiments C1-C3, the alcohol/ester stream comprises less than 5 wt. %, 3 wt. %, 2 wt. %, 1 wt. %, 0.5 wt. %, 0.1 wt. %, 500 ppm water, or 200 ppm water.

C5. The process of any of embodiments C1-C4, wherein the formate ester mixture comprises at least 20 wt. %, 25 wt. %, 45 wt. %, 50 wt. %, 75 wt. %, or 90 wt. % formate ester of the carrier alcohol.

C6. The process of any of embodiments C1-C5, wherein a molar ratio of water:formate ester of the carrier alcohol fed to the hydrolysis zone ranges from 1:1 to 3:1, or 1.1:1 to 2.5:1, or 1.2:1 to 2:1.

C7. The process of any of embodiments C1-C6, wherein the carrier alcohol is selected from the group consisting of $C_5$ to $C_{12}$ or $C_5$ to $C_{10}$ secondary and tertiary alcohols.

C8. The process of any of embodiments C1-C6, wherein the carrier alcohol is selected from the group consisting of 1-popoxy-2-propanol, 1-ethoxy-2-propanol, [2,2,2]-bicyclo-1,4-octanediol, adamantane-1,3,5,7-tetraol, and adamantine-1,3-diol; or the carrier alcohol is selected from the group consisting of 1-popoxy-2-propanol and 1-ethoxy-2-propanol; or the carrier alcohol is selected from the group consisting of [2,2,2]-bicyclo-1,4-octanediol, adamantane-1,3,5,7-tetraol, and adamantine-1,3-diol; or the carrier alcohol is 1-popoxy-2-propanol; or the carrier alcohol is 1-ethoxy-2-propanol; or the carrier alcohol is [2,2,2]-bicyclo-1,4-octanediol; or the carrier alcohol is adamantane-1,3,5,7-tetraol; or the carrier alcohol is adamantine-1,3-diol.

C9. The process of any of embodiments C1-C8, wherein the carrier alcohol has a boiling point temperature higher than a boiling point temperature of the formate ester of the carrier alcohol at an operating pressure of the catalyst separation zone.

C10. The process of any of embodiments C1-C9, wherein the hydrolysis zone operates at a temperature from 40° C. to 140° C. and at a pressure from 1 bara to 40 bara.

C11. The process of any of embodiments C1-C10, wherein the hydrolysis zone comprises a hydrolysis catalyst.

C12. The process of any of embodiments C1-C11, wherein an overall conversion of formate ester of the carrier alcohol in the formate ester mixture to formic acid in the formic acid product ranges from 40% to 90%, 50% to 90%, or 60% to 90%.

C13. The process of any of embodiments C1-C12, wherein the formate ester of the carrier alcohol in the hydrolysis effluent further hydrolyzes in the distillation column.

C14. The process of any of embodiments C1-C13, wherein an overall conversion of formate ester of the carrier alcohol to formic acid ranges from 2 to 40 percentage points higher than the hydrolysis conversion of formate ester of the carrier alcohol to formic.

C15. The process of any of embodiments C1-C14, wherein the first distillation column has a base temperature from 40° C. to 150° C., 45° C. to 125° C., or 45° C. to 100° C., and the operating pressure of the first distillation column ranges from 0.05 bara to 4 bara, 0.05 bara to 3 bara, or 0.1 bara to 2 bara.

C16. The process of any of embodiments C1-C15, wherein the first distillation column comprises from 5 to 40, 10 to 30, or 10 to 15 theoretical stages.

C17. The process of any of embodiments C1-C16, wherein a first distillate from the first distillation column comprises a higher weight percent of formic acid than a weight percent of formic acid in a formic acid/water azeotrope at the operating pressure of the first distillation column; the process further comprising d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and e) feeding the product purification column bottoms to the first distillation column.

C18. The process of any of embodiments C1-C17, further comprising removing a first bottoms from the first distillation column, and f) feeding the first bottoms to a clean-up column and removing the alcohol/ester stream as a clean-up column bottoms and removing a clean-up column distillate; and g) feeding the clean-up distillate to the first distillation column.

C19. The process of any of embodiments C1-C18, further comprising feeding the alcohol/ester stream to the DHC zone.

C20. The process of any of embodiments C1-C19, wherein the carrier alcohol feed comprises the alcohol/ester stream.

FIG. 1 represents a non-limiting embodiment of the present invention. Specifically, FIG. 1 illustrates a non-limiting process flow diagram of the production of formic acid via carbonylation of 1-propoxy-2-propanol.

Fresh feed 100 comprising 1-propoxy-2-propanol is fed to carbonylation zone 20. Carbon monoxide 102 is compressed in compressor 10 and compressed carbon monoxide 104 is fed to carbonylation zone 20. The process comprises carbonylating the 1-propoxy-2-propanol to produce 1-propoxy-2-propyl formate. Carbonylation effluent 106 comprises 1-propoxy-2-propyl formate, 1-propoxy-2-propanol, and a homogeneous catalyst. Carbonylation effluent 106 is fed to catalyst separation zone 30. Catalyst mixture 108 and formate ester mixture 114 are removed from catalyst separation zone 30. Catalyst mixture 108 is split into small catalyst purge 112 and catalyst recycle 110 which is fed back to the carbonylation zone. Catalyst mixture 108, catalyst purge 112, and catalyst recycle 110 comprise the homogeneous catalyst and 1-propoxy-2-propanol. Formate ester mixture 114 comprises 1-propoxy-2-propyl formate.

Formate ester mixture 114 and water 116 are fed to hydrolysis zone 40. In the hydrolysis zone, 1-propoxy-2-propyl formate is hydrolyzed and hydrolysis effluent 118 is removed. Hydrolysis effluent 118 comprises 1-propoxy-2-propyl formate, formic acid, and 1-propoxy-2-propanol. Hydrolysis effluent 118 is fed to (first) distillation column 50. Distillate 120 is removed from distillation column 50 and comprises a higher weight percent of formic acid than a weight percent of formic acid in a formic acid/water azeotrope at an operating pressure of distillation column 50. Bottoms 122 is removed from distillation column 50 and comprises 1-propoxy-2-propanol and less than 5 wt. % formic acid. Bottoms 122 is recycled back to carbonylation zone 20.

Figure 2:
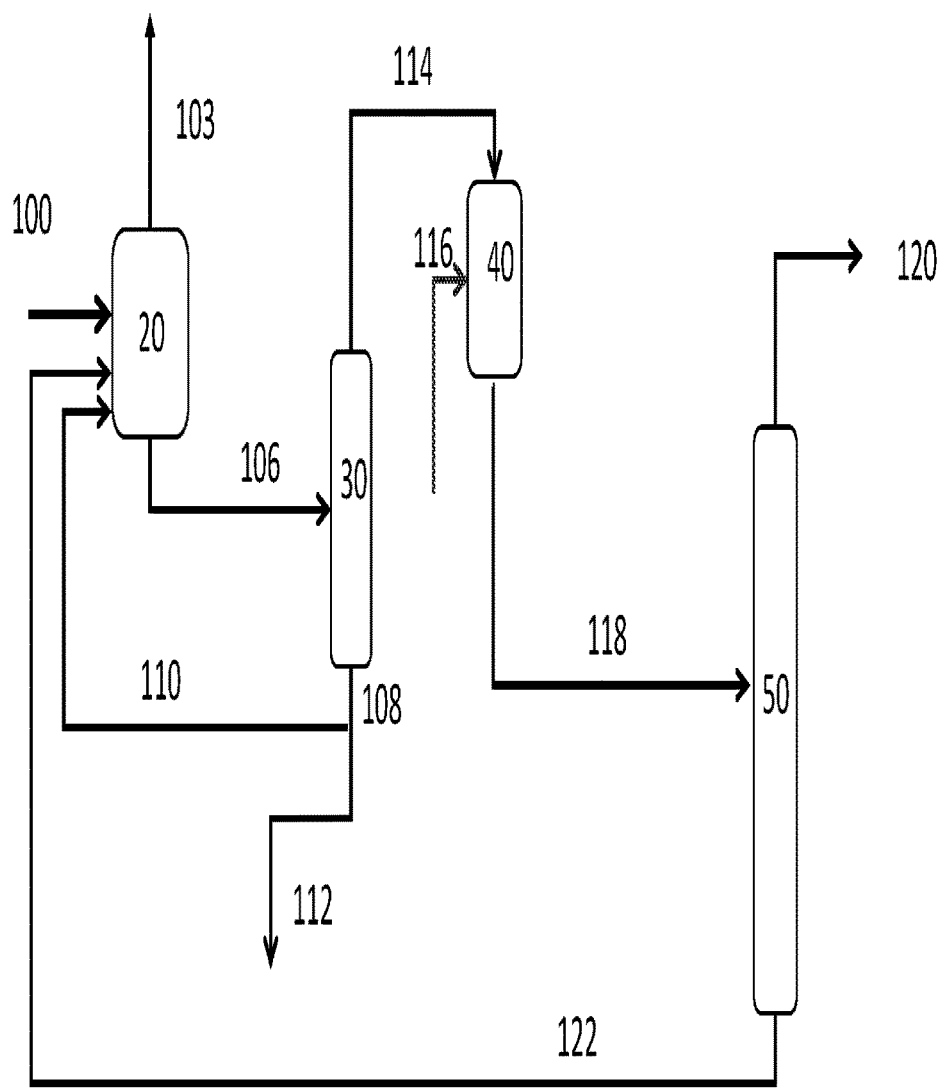
FIG. 2 illustrates a non-limiting process flow diagram of the production of formic acid via dehydrogenative coupling of methanol and 1-propoxy-2-propanol.

FIG. 2 represents a non-limiting embodiment of the present invention. Specifically, FIG. 2 illustrates a non-limiting process flow diagram of the production of formic acid via dehydrogenative coupling of methanol and 1-propoxy-2-propanol.

Methanol 100 is fed to dehydrogenative coupling (DHC) zone 20. Alcohol feed 122 and catalyst recycle 110 are also feed to DHC zone 20. The process comprises performing a DHC reaction of methanol with 1-propoxy-2-propanol to produce 1-propoxy-2-propyl formate and hydrogen. Hydrogen outlet 103 is removed from DHC zone 20. DHC effluent 106 comprises 1-propoxy-2-propyl formate, and a homogeneous catalyst. DHC effluent 106 is fed to catalyst separation zone 30. Catalyst mixture 108 and formate ester mixture 114 are removed from catalyst separation zone 30. Catalyst mixture 108 is split into small catalyst purge 112 and catalyst recycle 110 which is fed back to DHC zone 20. Catalyst mixture 108, catalyst purge 112, and catalyst recycle 110 comprise the homogeneous catalyst. Formate ester mixture 114 comprises 1-propoxy-2-propyl formate.

Formate ester mixture 114 and water 116 are fed to hydrolysis zone 40. In the hydrolysis zone, 1-propoxy-2-propyl formate is hydrolyzed and hydrolysis effluent 118 is removed. Hydrolysis effluent 118 comprises 1-propoxy-2-propyl formate, formic acid, and 1-propoxy-2-propanol. Hydrolysis effluent 118 is fed to (first) distillation column 50. The distillate 120 is removed from distillation column 50 and comprises a higher weight percent of formic acid than a weight percent of formic acid in a formic acid/water azeotrope at an operating pressure of distillation column 50. Bottoms 122 is removed from distillation column 50 and comprises 1-propoxy-2-propanol and less than 5 wt. % formic acid. In this illustration bottoms 122 becomes alcohol recycle 122 and is fed to DHC zone 20.

The invention can be further illustrated by the following examples of preferred embodiments thereof, although it will be understood that these examples are included merely for purposes of illustration and are not intended to limit the scope of the invention.

EXAMPLES

Abbreviations used in Examples and Tables are given below.
1P2P=1-propoxy-2-propanol
1P2PF=1-propoxy-2-propyl formate
DEG=Diethylene glycol
DEGDF=Diethylene glycol diformate
DEGMF=Diethylene glycol monoformate
DEGMME=Diethylene glycol monomethyl ether
DEGMME formate=Diethylene glycol monomethyl ether formate
EG=Ethylene glycol
EGDF=Ethylene glycol diformate
EGMF=Ethylene glycol monoformate
FA=Formic acid
MF=Methyl formate
ROH=Alcohol with R representing the remainder of the carrier alcohol 95 wt. % Formic acid, methyl formate, alcohols, diols, and alkanols were purchased and used without further processing.

Process samples were analyzed using a Shimadzu gas chromatograph (GC) Model 2010 (or equivalent) equipped with a heated split injector (250° C.) and a flame ionization detector (250° C.). A capillary GC column coated with 100% dimethylpolysiloxane (such as DB-1 or equivalent) with dimension of 60-meter×0.32-mm ID×1.0-micron film thickness was employed. Helium was used as the carrier gas with an initial column head pressure of 11.5 psi and an initial column flow of 1.30 mL/minute while the carrier gas linear velocity of 20 cm/second was maintained constant. The GC oven temperature program was as follows: the initial oven temperature was set at 50° C. and was held for 10 minutes, the oven was ramped up to 250° C. at 4° C./minute and was held at 250° C. for 15 minutes (the total run time was 45 mins). 1.0-uL of the prepared sample solution was injected with a split ratio of 40:1. EZ-Chrom Elite chromatography data system software was used for data acquisition and data processing. The sample preparation was done by weighing 0.03 g (accurate to 0.1 mg) of sample in a GC vial and adding 200.0-uL of ISTD solution (1% by volume of nonane in pyridine) and 1000-uL of BSTFA (N, O-bis(trimethylsilyl) trifluoroacetamide) with 1% TMCS (trimethylchlorosilane) to the GC vial. The content was heated at 80° C. for 30 minutes to ensure complete derivatization.

In order to calibrate the GC area counts to actual compositions, a response factor was determined independently for each component of interest. Samples of the components of interest with known concentrations were prepared and analyzed. The known concentrations were plotted against the GC area counts: the slope of this graph is the response factor. At least in part, because of the independent calibration of each component, the sum of GC wt. %'s does not always add to unity, due to errors in calibration.

The percentage of free formic acid is calculated as the moles of equilibrium formic acid divided by the sum of the moles of initial formic acid and alcohol formate ester, multiplied by 100. The molar equilibrium ratio, $K_x$, is calculated as $K_x=(x_{FA}*x_{OH})/(x_{FE}*x_{H2O})$. $x_{FA}$ is the mole fraction of formic acid, $x_{OH}$ is the mole fraction of the carrier alcohol, $x_{FE}$ is the mole fraction of the formate ester of the carrier alcohol and $x_{H2O}$ is the mole fraction of water.

All mole fractions are based upon measurement at equilibrium. Unless otherwise noted, $K_x$ for diol cases is calculated with $x_{OH}$ being the mole fraction of diol and $x_{FE}$ being the mole fraction of the monoformate plus the diformate.

Initial Screening Experiments

In order to approximate which formate esters would have more favorable hydrolysis equilibrium characteristics with a corresponding higher conversion of the formate esters of the carrier alcohols to formic acid, a series of screening experiments were conducted. Because the alcohols are more readily available than the corresponding formate esters, potential carrier alcohols and formic acid were mixed at elevated temperature and allowed to come to equilibrium. Those with more favorable equilibrium characteristics than that of methyl formate hydrolysis to formic acid and methanol were considered for further experimentation.

Example 1—Equilibration of Methanol with Formic Acid 5 grams of methanol was mixed initially with an equimolar amount of 95 wt. % formic acid (molar ratio of methanol to formic acid was 1/1 initially) and added to a sealed thick-walled vial. The vial was heated to 80° C. and held with mixing for 24 hours at the autogenous pressure to ensure equilibrium conversion. The resulting reaction products were sampled and analyzed by gas chromatography to determine composition. The percentage of the free formic acid present at equilibrium and the molar equilibrium ratio, $K_x$, were calculated from the analytical data and are presented in Table 1.

Examples 2-14—Equilibration of Primary, Secondary and Tertiary Alkanols with Formic Acid Example 1 was repeated with the alcohols listed in Table 1. The percentage of the free formic acid present at equilibrium and the molar equilibrium ratio, $K_x$, were calculated from the analytical data and are presented in Table 1. The molar hydrolysis equilibrium ratio and resulting percentage of free formic acid is much higher for secondary alcohols ($K_x$ from 0.71 to 149 and % free formic acid from 46% to 54%) and tertiary alcohols ($K_x$ from 13.6 to 14 and % free formic acid of 79%) as compared to methanol ($K_x$ of 0.18 and % free formic acid of 30%).

TABLE 1

Equilibration results for Examples 1-14

| Example | Alcohol (ROH) | ROH Type | Kx | % free formic acid at equilibrium |
|---|---|---|---|---|
| 1 | Methanol | primary | 0.18 | 30% |
| 2 | Isopropanol | secondary | 0.71 | 46% |
| 3 | n-butanol | primary | 0.29 | 35% |
| 4 | Isobutanol | primary | 0.32 | 36% |
| 5 | sec-butanol | secondary | 0.70 | 46% |
| 6 | Tert-butanol | tertiary | 14.0 | 79% |
| 7 | 1-methylcyclohexanol | tertiary | 13.6 | 79% |
| 8 | 2,4-dimethyl-3-pentanol | secondary | 1.05 | 51% |
| 9 | 1-ethoxy-2-propanol | secondary | 1.37 | 54% |
| 10 | 1-methoxy-2-propanol | secondary | 1.35 | 54% |
| 11 | 1-propoxy-2-propanol | secondary | 1.20 | 52% |
| 12 | 1-phenoxy-2-propanol | secondary | 1.07 | 51% |
| 13 | DEG monomethyl ether | primary | 0.80 | 47% |
| 14 | Phenol | secondary | 149 | 92% |

Example 15—Equilibration of Ethylene Glycol and Formic Acid 5 grams of the ethylene glycol was mixed initially with an equimolar amount of 95 wt. % formic acid (molar ratio of ethylene glycol to formic acid was 1/2 initially which corresponds to an OH/formic acid ratio of 1/1 as each ethylene glycol has two OH groups) and added to a sealed thick-walled vial. The vial was heated to 60° C. and held with mixing for 24 hours at the autogenous pressure to ensure equilibrium conversion. The resulting reaction products were sampled and analyzed by gas chromatography to determine composition. The percentage of the free formic acid present at equilibrium and the molar equilibrium ratio, $K_x$, were calculated from the analytical data and are presented in Table 2.

Examples 16-18—Equilibration of Diols with Formic Acid

Example 15 was repeated with the diols listed in Table 2. The percentage of the free formic acid present at equilibrium and the molar equilibrium ratio, $K_x$, were calculated from the analytical data and are presented in Table 2. 1,2-propanediol, Example 16, with its secondary OH group, had a $K_x$ of 0.71 and a percentage free formic acid of 46% as compared to methanol, Example 1, which had a $K_x$ of 0.18 and percentage free formic acid of 30%.

TABLE 2

Equilibration Results for Examples 15-18

| Example | Alcohol (ROH) | ROH Type | Kx | Percentage free formic acid at equilibrium |
|---|---|---|---|---|
| 15 | Ethylene glycol | primary | 0.18 | 29% |
| 16 | 1,2-propanediol | secondary | 0.71 | 46% |
| 17 | 1,3-propanediol | primary | 0.29 | 35% |
| 18 | Diethylene glycol | primary | 0.32 | 36% |

Example 19—Equilibration of 1-ethoxy-2-propanol 5 grams of the 1-ethoxy-2-proponal was mixed initially with an equimolar amount of 95 wt. % formic acid (molar ratio of 1-ethoxy-2-propanol to formic acid was 1.05/1 initially) and added to a sealed thick-walled vial. The vial was heated to 80° C. and held with mixing for 24 hours at the autogenous pressure to ensure equilibrium conversion. The resulting reaction product was sampled and analyzed by gas chromatography to determine composition. The percentage of the free formic acid present at equilibrium and the molar equilibrium ratio, $K_x$, were calculated from the analytical data and are presented in Table 3.

Examples 20-25—Equilibration of 1-alkoxy-2-alkanols with Formic Acid

Example 19 was repeated with the 1-alkoxy-2alkanols or methanol as listed in Table 3. Also, in Examples 20, 22, 24, and 25 water was added in the molar ratior given in Table 3. The percentage of the free formic acid present at equilibrium and the molar equilibrium ratio, $K_x$, were calculated from the analytical data and are presented in Table 3. The percentage of free formic acid is much higher for the 1-alkoxy-2-alkanols (54 to 70% free formic acid and $K_x$ from 1.17 to 1.75) compared to methanol (30 to 32% free formic acid and $K_x$ of 0.18 to 0.21), showing more favorable equilibrium hydrolysis for the 1-alkoxy-2-alkanols as compared to methanol.

TABLE 3

Equilibration results for Examples 19-25

| Example | Alcohol, ROH | Input ROH/ FA Molar ratio | Input ROH/ water Molar Ratio | Outlet Fraction as Free Formic Acid | Molar ratio at equilibrium, $K_x$ |
|---|---|---|---|---|---|
| 19 | 1-ethoxy-2-propanol | 1.05 | 0.00 | 59% | 1.55 |
| 20 | 1-ethoxy-2-propanol | 1.05 | 0.88 | 77% | 1.75 |
| 21 | 1-propoxy-2-propanol | 1.05 | 0.00 | 54% | 1.16 |
| 22 | 1-propoxy-2-propanol | 1.05 | 0.88 | 74% | 1.63 |
| 23 | 1-butoxy-2-propanol | 1.05 | 0.00 | 54% | 1.17 |
| 24 | 1-butoxy-2-propanol | 1.05 | 0.88 | 70% | 1.67 |
| Ex 1 | MeOH | 1.05 | 0.00 | 30% | 0.18 |
| 25 | MeOH | 1.05 | 0.88 | 32% | 0.21 |

Synthesis of Formate Esters

Various formate esters used in the hydrolysis examples were produced by carbonylating the corresponding alcohols or by esterifying the corresponding alcohols with formic acid. The method for producing the formate ester was chosen based upon the ease of making each particular formate ester.

Example P1. Preparation of Formate Ester Via Esterification of Alcohol with Formic Acid A number of formate esters were synthesized via formic acid-catalyzed esterification of alkanols with formic acid. The following procedure is representative of the synthesis procedure used herein. 500 grams of DEGMME and 217 grams of formic acid were charged to a 2-liter glass flask fitted with a glass vacuum-jacketed packed column (2.5 cm ID×60 cc length, Pro-Pak® hastelloy packing) Dean-Stark trap, heating mantle, nitrogen purge, 1-liter distillate receiver, and cooling water condenser. N-Hexane was added to the reaction flask (150 grams) and to the Dean-Stark trap. The mixture was brought to the boiling point, esterification commenced, and the water of reaction was removed as the n-hexane-water azeotrope. This azeotrope separated into two layers in the Dean-Stark trap, with the hexane layer returned to the column, and water removed periodically from the trap. The distillation was continued until water removal was complete (about 75 grams of water). The pot temperature was increased and the hexane removed from the pot. A total of 623 grams of DEGMME formate was produced, with a composition of 97 wt. % DEGMME formate, 2.8 wt. % DEGMME, 0.13 wt. % water, 0.7 wt. % formic acid, and less than 0.1 wt. % n-hexane by gas chromatography analysis.

Example P2—Carbonylation of Ethylene Glycol 150 grams of a solution of 2.5 wt. % of sodium salt of ethylene glycol (Na-EG) in ethylene glycol was prepared by slowly adding 1.50 grams of sodium metal to a magnetically stirred 500-ml glass flask containing 214.5 grams of chilled and thoroughly dried ethylene glycol (water content less than 0.1 wt. %). The reaction was complete when evolution of hydrogen gas ceased and the sodium metal was entirely dissolved. In three separate experiments, 50 grams of the thus prepared Na-EG solution was transferred to a 0.2-liter Hastelloy C276 autoclave, fitted with a heating mantle, magnetic drive agitator, CO and $CO_2$ gas supply lines. The autoclave was purged with dry nitrogen, followed by CO, then pressurized with CO, heated to the desired temperature, and stirred at 1000 rpm for 6 hours. The reactor was cooled to room temperature, CO vented, and then the vessel was pressurized with $CO_2$ to 1.04 MPa to neutralize the Na-EG catalyst and form insoluble sodium carbonate. The reactor contents were filtered to remove sodium carbonate. The product ethylene glycol formate mixture was analyzed by gas chromatography. Reaction conditions and compositions are given in Table 4.

TABLE 4

Carbonylation of ethylene glycol

| Test # | Temp, ° C. | CO pressure, MPa | Composition, wt. % | | | | |
|---|---|---|---|---|---|---|---|
| | | | Formic acid | Water | EGDF | EGMF | EG |
| P2-1 | 70.0 | 6.31 | 1.05 | 0.21 | 0.55 | 37.03 | 62.22 |
| P2-2 | 90.0 | 7.00 | 1.29 | 0.44 | 0.29 | 30.99 | 67.66 |
| P2-3 | 90.0 | 11.14 | 1.15 | 1.48 | 1.07 | 39.33 | 55.16 |

The formate esters synthesized, the general method of production, and the composition are given in Table 5.

TABLE 5

Formate Esters produced, synthesis method, and composition

| Ex # | Formate Ester | Method | GC composition (wt. %) |
|---|---|---|---|
| F1 | 1P2P formate | 2 | 97% 1P2P formate, 3% 1P2P |
| F2 | DEGMME formate | 1 | 97.0% DEGMME formate, 0.07% Formic acid, 0.13% water, 2.8 wt. % DEGMME |
| F3 | EG formate | 2 | 37.0% EGMF, 0.6% EGDF, 1.0% FA, 0.2% water, 62.2% EG |
| F4 | EG formate | 2 | 31.0% EGMF, 0.3% EGDF, 1.3% FA, 0.4% water, 67.7% EG |
| F5 | EG formate | 2 | 39.3% EGMF, 1.1% EGDF, 1.2% FA, 1.5% water, 55.2% EG |

TABLE 5-continued

Formate Esters produced, synthesis method, and composition

| Ex # | Formate Ester | Method | GC composition (wt. %) |
|---|---|---|---|
| F6 | DEGDF | 1 | 86 wt. % DEGDF, 0.055 wt. % formic acid, 0.19 wt. % water, 13.27 wt. % DEGMF |
| F7 | EG di/mono formate | 1 | 52.5% EGMF, 35.9% EGDF, 5.9% FA, 1.1% water, 5.1% EG |
| F8 | EG di/mono formate | 1 | 76.1% EGMF, 12.2% EGDF, 0.5% FA, 0.4% water, 10.8% EG |
| F9 | EG di/mono formate | 1 | 53.9% EGMF, 2.2% EGDF, 0.02% FA, 0.2% water, 44.0% EG |

Hydrolysis of Formate Esters

Example 26—Hydrolysis of 1-Propoxy-2-Propyl Formate

Water, 1-propoxy-2-propyl formate (F1 which was prepared by method P2), and a small amount of formic acid were added to sealed glass vials in the proportions given in Table 6. These vials were heated to 80° C. and held with mixing for 16 hours at the autogenous pressure to ensure equilibrium conversion. The resulting reaction product was sampled and analyzed by gas chromatography to determine composition. Conversion to free formic acid and the molar equilibrium ratio, $K_x$, were calculated as given above and are shown in Table 6.

Examples 27-31 Hydrolysis of Formate Esters

Example 26 was repeated with the formate ester and amounts of water as given in Table 6. Vials were heated to 80° C. and held with mixing for 24 hours at the autogenous pressure to ensure equilibrium conversion. The resulting reaction product was sampled and analyzed by gas chromatography to determine composition. Conversion to free formic acid and the molar equilibrium ratio, $K_x$, were calculated as given above and are shown in Table 6.

TABLE 6

Hydrolysis of formate esters Examples 26-31

|  | Ex 26 | Ex 27 | Ex 28 | Ex 29 | Ex 30 | Ex 31 |
|---|---|---|---|---|---|---|
| Formate | F1 | F1 | MF | MF | F2 | F2 |
| Temperature (° C.) | 80 | 80 | 80 | 80 | 60 | 60 |
| Input (g) | | | | | | |
| 95 wt. % formic acid | 0.21 | 0.19 | 0.21 | 0.19 | 0.0 | 0.0 |
| Water | 2.72 | 4.91 | 2.72 | 4.91 | 1.75 | 2.91 |
| formate | 22.07 | 19.91 | 9.1 | 16.4 | 10.0 | 10.0 |
| Water/formate molar ratio | 1/1 | 2/1 | 1/1 | 2/1 | 1.5/1 | 2.5/1 |
| Results | | | | | | |
| Conversion to free formic acid | 53% | 71% | 28% | 29% | 56% | 70% |
| Molar ratio at equilibrium, $K_x$ | 1.15 | 1.32 | 0.19 | 0.20 | 0.8 | 0.97 |

Examples 26-31 show a higher conversion to free formic acid for the hydrolysis of 1-propoxy-2-propyl formate (53% and 71% at 1/1 and 2/1 water to formate mole ratio, respectively) and diethylene glycol monomethyl ether formate (56% and 70% at 1/1 and 2/1 water to formate mole ratio, respectively) than for methyl formate (28% and 29% at 1/1 and 2/1 water to formate mole ratio, respectively).

Example 32—Hydrolysis of Diethylene Glycol Diformate Mixture

A diethylene glycol diformate (DEGDF) mixture, F6, was added with water to a sealed glass vial in the proportion given in Table 7. This vial was heated to 60° C. and held with mixing for 24 hours to ensure equilibrium conversion. The resulting reaction product was sampled and analyzed by gas chromatography to determine composition. Conversion of DEGDF, conversion of hydroxyl groups, overall conversion to free formic acid and the molar equilibrium ratios, $K_{x2-1}$ and $K_{x1-0}$, were calculated as given above.

Where:

$$K_{x2-1} = \frac{x_{FA} x_{DEGMF}}{x_{DEGDF} x_{water}} \text{ and } K_{x1-0} = \frac{x_{FA} x_{DEG}}{x_{DEGMF} x_{water}}$$

Example 33—Hydrolysis of Ethylene Glycol Formate Mixture 10.0 grams of Ethylene glycol formate mixture, F7, was added with 2.7 grams water to a sealed glass vial. These vials were heated to 60° C. and held with mixing for 24 hours to ensure equilibrium conversion. The resulting reaction products were sampled and analyzed by gas chromatography to determine composition. Conversion of EG diformate, overall conversion to free formic acid, and the molar equilibrium ratios, $K_{x2-1}$ and $K_{x1-0}$, were calculated as given above and are shown in Table 7.

$$K_{x2-1} = \frac{x_{FA} x_{EGMF}}{x_{EGDF} x_{water}} \text{ and } K_{x1-0} = \frac{x_{FA} x_{EG}}{x_{EGMF} x_{water}}$$

Where:

Examples 34-35—Hydrolysis of Ethylene Glycol Formate Mixtures

Example 33 was repeated with the formate mixtures as noted on Table 7. The resulting reaction products were sampled and analyzed by gas chromatography to determine composition. Conversion of EG diformate, overall conversion to free formic acid, and the molar equilibrium ratios, $K_{x2-1}$ and $K_{x1-0}$, were calculated as given above and shown in Table 7.

TABLE 7

Hydrolysis of diethylene glycol formate and ethylene glycol formate mixtures, Examples 32-35

|  | Ex 32 | Ex 33 | Ex 34 | Ex 35 |
|---|---|---|---|---|
| Formate Input, grams | F6 | F7 | F8 | F9 |
| Formate mixture | 10.0 | 10.0 | 10.0 | 10.0 |
| Water | 2.7 | 2.7 | 1.0 | 1.67 |
| Water/ester groups molar ratio | 1.3/1 | 1.3/1 | 1.5/1 | 1.5/1 |

TABLE 7-continued

Hydrolysis of diethylene glycol formate and ethylene glycol formate mixtures, Examples 32-35

|  | Ex 32 | Ex 33 | Ex 34 | Ex 35 |
|---|---|---|---|---|
| Results |  |  |  |  |
| Conversion of diformate | 73.6% | 80% | 64% | 37% |
| Overall conversion to free formic acid | 48% | 46% | 40% | 26% |
| Molar ratio at equilibrium, $K_{x2\text{-}1}$ | 1.34 | 4.77 | 5.9 | 7.8 |
| Molar ratio at equilibrium, $K_{x1\text{-}0}$ | 0.34 | 0.25 | 0.30 | 0.38 |

Examples 33-35 show that the hydrolysis of DEGDF and EG diformate is particularly favorable, while hydrolysis of DEGMF and EG monoformate is similar to that of methyl formate.

Separation of Formic Acid from Formate Ester and Water

Example 36—Distillation of Formic Acid from 1-Propoxy-2-Propyl Formate Hydrolysis Mixture Recovery of formic acid from a high-boiling formate ester hydrolysis mixture was demonstrated in a batch distillation. 59.7 grams of, 1-propoxy-2-propyl formate, F1, was mixed with 7.4 grams of water, heated to 80° C., and allowed to equilibrate for 12 hours to produce a hydrolysis mixture comprising, 20.3 wt. % formic acid, 3.0 wt. % water, 21.8 wt. % 1-propoxy-2-propyl formate, 54.8 wt. % 1-propoxy-2-propanol. Conversion of ester to free formic acid was 70%. This hydrolysis mixture was charged to a batch distillation column comprising a 0.2-liter glass flask fitted with a glass vacuum-jacketed packed column (1.2 cm ID×30 cc length, Heli-Pak hastelloy packing) reflux head, heating mantle, nitrogen purge, vacuum pump, and cooling water condenser. The mixture was brought to the boiling point at 0.13 bara (about 78° C.), the reflux head was set to 2/1 reflux and three successive distillate cuts were collected, weighed, and analyzed by gas chromatography. The distillation was stopped, allowed to cool, and the pot residue was collected, weighed, and analyzed by gas chromatography. Results are summarized in Table 8. A total of 9.7 grams of formic acid was collected in the three distillate cuts. This represents a 53% recovery of formic acid contained in the 1-propoxy-2-propyl formate carbonylation product charged to the hydrolysis step (76% of free formic acid in the feed). The remainder of free formic acid in the feed was either re-esterified or left in the pot residue.

Example 37—Distillation of Formic Acid from 1-propoxy-2-propyl formate Equilibration Mixture Recovery of formic acid from a high-boiling formate ester hydrolysis mixture was demonstrated in a batch distillation. The high boiling ester, 1-propoxy-2-propyl formate, was prepared by equilibration of a formic acid/1-propoxy-2-propanol mixture (140 grams of 98 wt. % formic acid, 2 wt. % water mixed with 360.8 grams of 1-propyl-2-propyl formate, alcohol/formic acid molar ratio of 1.02, held at 80° C. for 14 hours). 61% of the formic acid fed to the equilibration remained as free formic acid. 500.8 grams of the equilibration product (33.33 wt. % 1-propoxy-2-propanol formate, 45.31 wt. % 1-propoxy-2-propanol, 16.58 wt. % formic acid, 4.78 wt. % water; thus, 83.1 grams of free formic acid) was charged to a batch distillation column comprising a 1-liter glass flask fitted with a glass vacuum-jacketed packed column (2.54 cm ID×82.3 cm length, 0.635 cm ProPak® hastelloy packing) reflux head, heating mantle, nitrogen purge, vacuum pump, and cooling water condenser. The mixture was brought to the boiling point at 0.066 bara (about 65.6° C.), the reflux head was set to 3/1 to 10/1 reflux and five successive distillate cuts were collected, weighed, and analyzed by gas chromatography. The distillation was stopped, allowed to cool, and the pot residue was collected, weighed, and analyzed by gas chromatography. Results are summarized in Table 8. A total of 9.7 grams of formic acid were collected in the five distillate cuts. This represents a 54% recovery of formic acid contained in the 1-propoxy-2-propyl formate mixture charged to the hydrolysis step. An additional 11.6 grams of free formic acid remained in the residue. Overall, 84.3 grams of free formic acid were accounted for between the distillate cuts and the residue, (62% of input formyl moieties) indicating that little further hydrolysis or back esterification occurred in the distillation.

TABLE 8

Batch distillation of formic acid from 1-propoxy-2-propyl formate, 1-propoxy-2-propanol, and water

|  | Temp, ° C. | | Mass | Composition, wt. % | | | |
|---|---|---|---|---|---|---|---|
|  | Dist. | Base | Grams | Formic acid | Water | 1P2PF | 1P2P |
| EX 36 |  |  |  |  |  |  |  |
| Feed Mixture |  |  | 67.1 | 20.34 | 3.02 | 21.83 | 54.81 |
| Cut 1 | 58.4 | 78.2 | 10.7 | 78.22 | 17.18 | 1.03 | 0.24 |
| Cut 2 | 88.4 | 96.6 | 2.7 | 43.14 | 19.53 | 19.54 | 15.53 |
| Cut 3 | 89.1 | 97.4 | 0.8 | 24.00 | 8.24 | 29.97 | 35.89 |
| Pot Residue |  |  | 49.6 | 2.86 | 0.16 | 36.72 | 60.25 |
| Ex 37 |  |  |  |  |  |  |  |
| Cut 1 | 34.9 | 65.6 | 14.1 | 97.2% | 2.8% | 0.0% | 0.0% |
| Cut 2 | 30.0 | 70.6 | 14.9 | 98.6% | 1.4% | 0.0% | 0.0% |
| Cut 3 | 38.0 | 72.5 | 9.7 | 95.9% | 4.1% | 0.1% | 0.0% |
| Cut 4 | 39.9 | 75.9 | 31.3 | 73.0% | 26.0% | 0.6% | 0.3% |
| Cut 5 | 39.6 | 76.2 | 17.6 | 69.2% | 29.3% | 0.9% | 0.5% |
| Pot Residue |  |  | 388.3 | 3.0% | 0.5% | 34.2% | 62.3% |

Examples 38 & 39—Continuous Distillation of Formic Acid from 1-propoxy-2-propyl formate Hydrolysis Mixture These examples illustrate the continuous distillative recovery of formic acid from a mixture resulting from the hydrolysis of 1P2P formate. A high boiling ester mixture comprising 97 wt. % 1-propoxy-2-propyl formate and 3 wt. % 1-propoxy-2-propanol, was prepared by the carbonylation of 1-propoxy-2-propanol as in F1 of Table 5. The carbonylation effluent was mixed with water and a small amount of formic acid, and hydrolyzed at 90° C. for a specified amount of time. The hydrolysis effluent was cooled and fed continuously to a distillation apparatus to recover formic acid. The distillation apparatus comprised a 1-liter glass flask fitted with a glass vacuum-jacketed packed column (2.54 cm ID×46 cm length, 0.635 cm ProPak® hastelloy packing) reflux head, heating mantle, nitrogen purge, vacuum pump, and cooling water condenser. The feed entered the column at room temperature, at 2 ml/min rate, at a point 16 cm from the bottom of the vacuum-jacketed column section. The vacuum pump was set to give a column head pressure of 0.067 bara. At this pressure, the formic acid/water azeotrope is about 60 wt. % formic acid/40 wt. % water. Heat was applied electrically to the base and boilup generated as material entered the reboiler pot. The reflux head was set to 3/1 to 10/1 reflux and distillate and bottoms streams were collected continuously. These streams were weighed, and analyzed by gas chromatography.

Example 38—Low Hydrolysis Conversion—Formic Acid Concentration Lower than in the Formic Acid/Water Azeotrope at Distillation Pressure 615 grams of high-boiling 1P2P formate ester carbonylation effluent was mixed with 80.1 grams of water, and 5.8 grams of 95 wt. % formic acid/5 wt. % water (1.09/1 moles water/mole ester). This mixture was held with stirring for 2 hours at 90° C., giving a hydrolysis effluent comprising 4.6 wt. % formic acid, 65 wt. % 1P2P formate, 20.8 wt. % 1P2P, and 9.5 wt. % water. About 14.8 percent of the 1P2P formate was converted to free formic acid and 1P2P, resulting in 33 wt. %/67 wt. % formic acid/water on a solvent free basis. This formic acid content is less than the amount of formic acid in the formic acid/water azeotrope (60 wt. % 40 wt. %) at the distillation pressure of 50 torr. The hydrolysis effluent was then distilled in the column described above at a reflux ratio of 3/1. The total collected distillate was analyzed by gas chromatography. The bottoms was sampled and analyzed by gas chromatography. Results are given in Table 9. No additional conversion of formate ester occurred during the distillation operation. 98.8% of the free formic acid in the hydrolysis effluent was recovered in the distillate, but the distillate was contaminated with almost 26% 1P2P and 1P2P formate, and the solvent free composition of the distillate was 28 wt. % formic acid/72 wt. % water.

Example 39—Higher Hydrolysis Conversion—Formic Acid Concentration Lower than in the Formic Acid/Water Azeotrope at Distillation Pressure 636 grams of high-boiling 1P2P formate ester carbonylation effluent was mixed with 82.7 grams of water, and 6.2 grams of 95 wt. % formic acid/5 wt. % water (1.09/1 moles water/mole ester). This mixture was held with stirring for 12 hours at 90° C., giving a hydrolysis effluent comprising 10.9 wt. % formic acid, 40.8 wt. % 1P2P formate, 41.2 wt. % 1P2P, and 6.9 wt. % water. About 36.2% of the 1P2P formate was converted to free formic acid and 1P2P, resulting in 62 wt. %/38 wt. % formic acid/water on a solvent free basis. The formic acid concentration is more than the formic acid concentration in the formic acid/water azeotrope (60 wt. %/40 wt. %) at the distillation pressure of 50 torr. The hydrolysis effluent was then distilled in the column described above at a reflux ratio of 4/1. A total of 697.43 grams of hydrolysis effluent was fed to the column. The total collected distillate was analyzed by gas chromatography. The bottoms was sampled and analyzed by gas chromatography. Results are given in Table 9. Additional formate ester was hydrolyzed in the column, with an overall conversion to free formic acid created of about 66%. About 82% of the free formic acid created in the hydrolysis and distillation was recovered in the distillate, and on a solvent free basis, the distillate was 67 wt. % formic acid/33 wt. % water.

TABLE 9

Examples 38 and 39

| | Feed | Distillate | Bottoms |
|---|---|---|---|
| Example 38 | | | |
| Temperature, ° C. | 22° C. | 39-42.5° C. | 86° C. |
| Mass, grams | 715.97 | 120.40 | 595.57 |
| Wt. % | | | |
| Formic acid | 4.6% | 27.3% | 0.1% |
| 1P2P formate | 65.0% | 18.1% | 74.5% |
| 1P2P | 20.8% | 7.6% | 23.5% |
| Water | 9.5% | 46.9% | 2.0% |
| unknowns | 0.1% | 0.0% | 0.1% |
| Example 39 | | | |
| Temperature, ° C. | 22° C. | 42.8° C. | 84.5° C. |
| Mass, grams | 697.4 | 133.6 | 573.0 |
| Wt. % | | | |
| Formic acid | 10.9% | 67.3% | 3.5% |
| 1P2P formate | 40.8% | 0.3% | 31.0% |
| 1P2P | 41.2% | 0.3% | 65.1% |
| Water | 7.0% | 32.1% | 0.3% |
| unknowns | 0.1% | 0.0% | 0.1% |

Example 40—Computer Simulation of the Distillation/Hydrolysis of an Ethylene Glycol Formate Mixture The distillation/hydrolysis of ethylene glycol monoformate (EGMF) to produce concentrated formic acid (FA) in a single reactive distillation column was modeled with a process simulator, using the vapor pressure and activity coefficient model parameters given in Table 10 and 11. Parameters held constant included:

- distillate concentration at 99 wt. % formic acid and 1 wt. % water,
- 20 ideal stages,
- equilibrium achieved on each stage with $K_x=0.38$, assumed constant,
- ester feed entered on stage 10 from the bottom, and
- water feed entered on stage 3 from the bottom.

Column pressure and the feed ratio of water to ester feed were varied. The simulation determined expected conversion of formate ester and underflow composition. To achieve reaction equilibrium in a physical distillation column at the operating pressures and temperatures, a catalyst would likely need to be used. Results are shown in Table 12. This example illustrates that it is possible to produce high formic acid concentrations by combined hydrolysis/distillation (hydrolysis of ethylene glycol monoformate and distillation of high-purity formic acid) in a single reactive distillation column.

TABLE 10

Vapor pressure constants

| Constant | Water | FA | EG | EGMF |
|---|---|---|---|---|
| A | 73.649 | 43.8066 | 84.09 | 25.46176 |
| B | −7258.2 | −5131.03 | −10411 | −6314.95 |
| C | −7.3037 | −3.18777 | −8.1976 | 0 |
| D | 4.17E−06 | 2.3782E−06 | 1.65E−18 | 0 |
| E | 2 | 2 | 6 | 0 |

$P^{sat} = \exp(A + B/T + C * \ln T + D * T^E)$, in KPa and T in kelvin

TABLE 11

Wilson Parameters

| | Comp 1 | | | | | |
|---|---|---|---|---|---|---|
| | Water | Water | water | FA | FA | EG |
| | | | Comp 2 | | | |
| | FA | EG | EGMF | EG | EGMF | EGMF |
| $a_{12}$ | 0.741226 | 1.1308 | 1.419277 | 0.3882 | 0.678001 | 0.2898 |
| $a_{21}$ | −0.74123 | −1.1308 | −1.41928 | −0.3882 | −0.678 | −0.2898 |
| $b_{12}$ | −276.194 | −409.3213 | −595.57 | 557.2854 | −77.8753 | 106.0456 |
| $b_{21}$ | 437.8245 | 438.0452 | −505.653 | −2031.9791 | −73.6109 | −309.4109 |

Wilson interaction parameter has the form of $u_{ij} = \exp(a_{ij} + b_{ij}/T)$

TABLE 12

Simulation results with Distillate composition held at 99 wt. % formic acid and 1 wt. % water

| | | Feed molar | | Bottoms Composition | |
|---|---|---|---|---|---|
| Case # | Pressure MPa | ratio W/EGMF | % Conversion | wt. % EG | wt. % EGMF |
| Case 1 | 0.101 | 0.113 | 11% | 7.8% | 92.2% |
| Case 2 | 0.027 | 0.277 | 27% | 20.3% | 79.7% |
| Case 3 | 0.010 | 0.605 | 59% | 49.8% | 50.2% |

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A process for recovering formic acid from a formate ester mixture, wherein the process comprises
   a) feeding the formate ester mixture and water to a hydrolysis zone, wherein the formate ester mixture comprises a formate ester of a carrier alcohol and the carrier alcohol;
   b) hydrolyzing the formate ester mixture in the hydrolysis zone to produce a hydrolysis effluent comprising the formate ester of the carrier alcohol, formic acid, and the carrier alcohol; and
   c) feeding the hydrolysis effluent to a distillation zone and removing a formic acid product and an alcohol/ester stream, wherein the formic acid product comprises greater than 75 wt. % formic acid and the alcohol/ester stream comprises less than 5 wt. % formic acid,
wherein the distillation zone comprises a first distillation column and the hydrolysis effluent is fed to the first distillation column,
wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope, with (1)-(3) being satisfied at an operating pressure of the first distillation column, and
wherein the carrier alcohol is selected from the group consisting of ethylene glycol, 1,2-propanediol, 1,3-propanediol, 1,2-butanediol, 1,3-butanediol, 2,3-butanediol, 1,4-butanediol, 1,2-cyclohexanediol, 1,3-cyclohexanediol, 1,4-cyclohexanediol, 1,2-phenylenedimethanol, 1,3-phenylenedimethanol, 1,4-phenylenedimethanol, 1,2-cyclohexanedimethanol, 1,3-cyclohexanedimethanol, 1,4-cyclohexanedimethanol, 2,2,4-trimethylpentane-1,3-diol, glycerol, trimethylolethane, trimethylolpropane, trimethylolbutane, diethylene glycol, triethylene glycol, diethylene glycol monomethyl ether, diethylene glycol monoethyl ether, diethylene glycol monopropyl ether, diethylene glycol monobutyl ether, 1-ethoxy-2-propanol, 1-propoxy-2-propanol, 1-butoxy-2-propanol, 2-ethoxy-1-propanol, 2-propoxy-1-propanol, 2-butoxy-1-propanol, ethylene glycol monoformate, diethylene glycol monoformate, 2-hydroxypropylformate, [2,2,2]-bicyclo-1,4-octanediol, adamantine-1,3,5,7-tetraol, and adamantane-1,3-diol.

2. The process of claim 1, wherein the formic acid product comprises greater than 95 wt. % formic acid.

3. The process of claim 1, wherein the alcohol/ester stream comprises less than 0.5 wt. %, formic acid and less than 200 ppm water.

4. The process of claim 1, wherein the formate ester mixture comprises at least 50 wt. % formate ester of the carrier alcohol.

5. The process of claim 1, wherein a molar ratio of water:formate ester of the carrier alcohol fed to the hydrolysis zone ranges from 1:1 to 3:1.

6. The process of claim 1, wherein the formate ester of the carrier alcohol is selected from the group consisting of formate ester of ethylene glycol, formate ester of diethylene glycol, formate ester of diethylene glycol monomethyl ether, formate ester of 1,2-propanediol, formate ester of 1-propoxy-2-propanol, formate ester of 2-hydroxy-propanol, formate ester of 1-ethoxy-2-propanol and formate ester of 1 butoxy-2-propanol and the carrier alcohol is selected from the group consisting of ethylene glycol, diethylene glycol, diethylene glycol monomethyl ether, 1,2-propanediol, 1-propoxy-2-propanol, 2-hydroxy-propanol, 1-ethoxy-2-propanol and 1-butoxy-2-propanol.

7. The process of claim 1, wherein a first distillate from the first distillation column comprises a higher weight percent of formic acid than a weight percent of formic acid in a formic acid/water azeotrope at the operating pressure of the first distillation column; the process further comprising
   d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and e) feeding the product purification column bottoms to the first distillation column.

8. The process of claim 1 wherein an overall conversion of the formate ester of the carrier alcohol in the formate ester mixture to formic acid in the formic acid product ranges from 40% to 90%.

9. The process of claim 1, wherein the first distillation column has a base temperature from 60° C. to 150° C., the operating pressure of the first distillation column ranges from 0.4 bara to 4 bara, and the first distillation column comprises from 10 to 40 theoretical stages.

10. A process for producing formic acid, wherein the process comprises,
  a) feeding carbon monoxide, a fresh feed, and a catalyst feed to a carbonylation zone, wherein the fresh feed comprises a carrier alcohol, carbonylating the carrier alcohol to produce a formate ester of the carrier alcohol, and removing a carbonylation effluent comprising the formate ester of the carrier alcohol, the carrier alcohol, and a homogeneous catalyst;
  b) feeding the carbonylation effluent to a catalyst separation zone and removing a catalyst mixture and a formate ester mixture, wherein the catalyst mixture comprises the homogeneous catalyst and the carrier alcohol, and wherein the formate ester mixture comprises the formate ester of the carrier alcohol;
  c) feeding the formate ester mixture and water to a hydrolysis zone, hydrolyzing the formate ester of the carrier alcohol, and removing a hydrolysis effluent comprising the formate ester of the carrier alcohol, formic acid, and the carrier alcohol; and
  d) feeding the hydrolysis effluent to a distillation zone and removing a formic acid product and an alcohol/ester stream, wherein the formic acid product comprises greater than 75 wt. % formic acid and the alcohol/ester stream comprises less than 5 wt. % formic acid;
wherein the distillation zone comprises a first distillation column and the hydrolysis effluent is fed to the first distillation column,
wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope, with (1)-(3) being satisfied at the operating pressure of the first distillation column, and
wherein the carrier alcohol is selected from the group consisting of ethylene glycol, 1,2-propanediol, 1,3-propanediol, 1,2-butanediol, 1,3-butanediol, 2,3-butanediol, 1,4-butanediol, 1,2-cyclohexanediol, 1,3-cyclohexanediol, 1,4-cyclohexanediol, 1,2-phenylenedimethanol, 1,3-phenylenedimethanol, 1,4-phenylenedimethanol, 1,2-cyclohexanedimethanol, 1,3-cyclohexanedimethanol, 1,4-cyclohexanedimethanol, 2,2,4-trimethylpentane-1,3-diol, glycerol, trimethylolethane, trimethylolpropane, trimethylolbutane, diethylene glycol, triethylene glycol, diethylene glycol monomethyl ether, diethylene glycol monoethyl ether, diethylene glycol monopropyl ether, diethylene glycol monobutyl ether, 1-ethoxy-2-propanol, 1-propoxy-2-propanol, 1-butoxy-2-propanol, 2-ethoxy-1-propanol, 2-propoxy-1-propanol, 2-butoxy-1-propanol, ethylene glycol monoformate, diethylene glycol monoformate, 2-hydroxypropylformate, [2,2,2]-bicyclo-1,4-octanediol, adamantine-1,3,5,7-tetraol, and adamantane-1,3-diol.

11. The process of claim 10, wherein the formic acid product comprises greater than 95 wt. %, formic acid and the alcohol/ester stream comprises less than 0.5 wt. % formic acid and less than 200 ppm water, and the process further comprises feeding the alcohol/ester stream to the carbonylation zone in step a).

12. The process of claim 10, wherein the formate ester mixture comprises at least 50 wt. % formate ester of the carrier alcohol.

13. The process of claim 10, wherein a molar ratio of water:formate ester of the carrier alcohol fed to the hydrolysis zone ranges from 1:1 to 3:1.

14. The process of claim 10, wherein the carrier alcohol is selected from the group consisting of ethylene glycol; diethylene glycol; diethylene glycol monomethyl ether; 1,2-propane diol; 1-propoxy-2-propanol; 2-hydroxy-propanol; 1-ethoxy-2propanol, and 1-butoxy-2-propanol.

15. The process of claim 10, wherein a first distillate from the first distillation column comprises a higher weight percent of formic acid than a weight percent of formic acid in a formic acid/water azeotrope at the operating pressure of the first distillation column; the process further
  d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and
  e) feeding the product purification column bottoms to the first distillation column.

16. The process of claim 10, wherein the first distillation column has a base temperature from 60° C. to 150° C., the operating pressure of the first distillation column ranges from 0.4 bara to 4 bara, and the first distillation column comprises from 10 to 40 theoretical stages.

17. A process for producing formic acid, wherein the process comprises,
  a) feeding methanol, an alcohol feed and a catalyst recycle to a dehydrogenative coupling (DHC) zone, wherein the alcohol feed comprises a carrier alcohol and less than 1 wt. % water, performing a DHC reaction of methanol with the carrier alcohol to produce a formate ester of the carrier alcohol, and removing a DHC effluent comprising the formate ester of the carrier alcohol and a homogeneous catalyst;
  b) feeding the DHC effluent to a catalyst separation zone and removing the catalyst recycle and a formate ester mixture, wherein the catalyst recycle comprises the homogeneous catalyst, and wherein the formate ester mixture comprises the formate ester of the carrier alcohol;
  c) feeding the formate ester mixture and water to a hydrolysis zone, hydrolyzing the formate ester of the carrier alcohol, and removing a hydrolysis effluent comprising the formate ester of the carrier alcohol, formic acid, and the carrier alcohol; and
  d) feeding the hydrolysis effluent to a distillation zone and removing a formic acid product and an alcohol/ester stream, wherein the formic acid product comprises greater than 75 wt. % formic acid and the alcohol/ester stream comprises less than 5 wt. % formic acid;
wherein the carrier alcohol is selected from the group consisting of $C_5$ to $C_{14}$ secondary and tertiary alcohols, wherein the distillation zone comprises a first distillation column and the hydrolysis effluent is fed to the first distillation column, wherein (1) each of the formate ester of the carrier alcohol, the carrier alcohol, and any azeotrope formed by the formate ester of the carrier alcohol and the carrier alcohol has a boiling point temperature higher than the formic acid/water azeotrope boiling point temperature, (2) the formate ester of the carrier alcohol and formic acid do not form an azeotrope, and (3) the carrier alcohol and formic acid do not form an azeotrope, with (1)-(3) being satisfied at an operating pressure of the first distillation column, and wherein the carrier alcohol is selected from the group consisting of 1-propoxy-2-propanol and 1-ethoxy-2-propanol.

18. The process of claim 17, wherein the formic acid product comprises greater than 95 wt. %, formic acid, the alcohol/ester stream comprises less than 0.5 wt. % formic acid and less than 200 ppm water, and the carrier alcohol feed comprises the alcohol/ester stream.

19. The process of claim 17, wherein a molar ratio of water:formate ester of the carrier alcohol fed to the hydrolysis zone ranges from 1:1 to 3:1.

20. The process of claim 17, wherein a first distillate from the first distillation column comprises a higher weight percent of formic acid than a weight percent of formic acid in a formic acid/water azeotrope at the operating pressure of the first distillation column; the process further comprises
  d) feeding the first distillate to a product purification column and removing the formic acid product as a product purification column distillate and removing a product purification column bottoms comprising formic acid in an amount within 7 weight percentage points of an amount of formic acid in a formic acid/water azeotrope at an operating pressure of the product purification column; and
  e) feeding the product purification column bottoms to the first distillation column.

* * * * *